US008993552B2

(12) United States Patent
Grembecka et al.

(10) Patent No.: US 8,993,552 B2
(45) Date of Patent: Mar. 31, 2015

(54) COMPOSITIONS AND METHODS FOR TREATMENT OF LEUKEMIA

(75) Inventors: Jolanta Grembecka, Charlottesville, VA (US); Tomasz Cierpicki, Charlottesville, VA (US); Jay Hess, Ann Arbor, MI (US)

(73) Assignees: The Regents of The University of Michigan, Ann Arbor, MI (US); University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 12/875,968

(22) Filed: Sep. 3, 2010

(65) Prior Publication Data

US 2011/0065690 A1    Mar. 17, 2011

Related U.S. Application Data

(60) Provisional application No. 61/240,102, filed on Sep. 4, 2009.

(51) Int. Cl.
*A61K 31/33*    (2006.01)
*A61K 31/519*   (2006.01)
*A61K 31/5513*  (2006.01)

(52) U.S. Cl.
CPC .......... *A61K 31/519* (2013.01); *A61K 31/5513* (2013.01)
USPC ....................................................... 514/183

(58) Field of Classification Search
CPC ............................. A61K 31/519; C07D 495/04
USPC ........................................................ 514/183
See application file for complete search history.

(56) References Cited

U.S. PATENT DOCUMENTS

| | | | |
|---|---|---|---|
| 6,849,638 B2 | 2/2005 | Stolle et al. | |
| 2003/0119829 A1 | 6/2003 | Stolle et al. | |
| 2003/0153556 A1* | 8/2003 | Levy et al. ................... | 514/218 |
| 2005/0123906 A1 | 6/2005 | Rana | |
| 2006/0025406 A1 | 2/2006 | Zembower et al. | |
| 2006/0281769 A1 | 12/2006 | Baumann et al. | |
| 2006/0281771 A1 | 12/2006 | Baumann et al. | |
| 2008/0293699 A1 | 11/2008 | Reed et al. | |
| 2009/0163545 A1 | 6/2009 | Goldfarb | |

FOREIGN PATENT DOCUMENTS

| | | |
|---|---|---|
| EP | 1382603 | 9/2008 |
| JP | 10-330377 | 12/1998 |
| WO | 99/65909 | 12/1999 |
| WO | 99/65909 A1 | 12/1999 |
| WO | 02/088138 A1 | 11/2002 |
| WO | 03022214 A2 | 3/2003 |
| WO | 2004030671 A2 | 4/2004 |
| WO | 2004030672 A1 | 4/2004 |
| WO | 2005/020897 A2 | 10/2005 |
| WO | 2006/135630 A1 | 12/2006 |
| WO | 2006/135636 A1 | 12/2006 |
| WO | 2007026024 A2 | 3/2007 |
| WO | WO2007/115822 | 10/2007 |
| WO | 2008/107320 A1 | 9/2008 |
| WO | 2008114275 A2 | 9/2008 |
| WO | 2009/017838 A2 | 2/2009 |
| WO | 2009/064388 A2 | 5/2009 |
| WO | 2010030757 A2 | 3/2010 |
| WO | 2011003418 A1 | 1/2011 |

OTHER PUBLICATIONS

U.S. Appl. No. 61/240,102, filed Sep. 4, 2009, Grembecka et al.
Agarawal et al., "Menin molecular interactions: insights into normal functions and tumorigenesis," Horm Matab Res, 37(6), pp. 369-374 (2005).
Chen et al., "The tumor suppressor menin regulates hematopoiesis and myeloid transformation by influencing Hox gene expression," Proc Natl Acad Sci USA, 103(4), pp. 1018-1023 (2006).
Cox et al., "Chromosomal aberration of the 11q23 locus in acute leukemia and frequency of MLL gene translocation: results in 378 adult patients," Am J Clin Pathol, 122(2), pp. 298-306 (2004).
Eguchi et al., "The role of the MLL gene in infant leukemia," Int J Hematol, 78(5), pp. 390-401 (2003).
Martin et al., Remington's Pharmaceutical Sciences, 15th ed., Mack Publ. Co., Easton, PA (1975).
Marx, "Molecular genetics of multiple endocrine neoplasia types 1 and 2," Nat Rev Cancer, 5(5), pp. 367-75 (2005).
Mayer et al. "Group epitope mapping by saturation transfer difference NMR to identify segments of a ligand in direct contact with a protein receptor," J Am Chem Soc, 123(25), pp. 6108-6117 (2001).
Mosmann et al., "Rapid colorimetric assay for cellular growth and survival: application to proliferation and cytotoxicity assays," J Immunol Methods, 65, (1-2), pp. 55-63 (1983).
Slany, "When epigenetics kills: MLL fusion proteins in leukemia," Hematol Oncol, 23(1), pp. 1-9 (2005).
Sorensen et al., "Molecular rearrangements of the MLL gene are present in most cases of infant acute myeloid leukemia and are strongly correlated with monocytic or myelomonocytic phenotypes," J Clin Invest, 93(1), pp. 429-437 (1994).
Yokoyama et al., "The menin tumor suppressor protein is an essential oncogenic cofactor for MLL-associated leukemogenesis," Cell, 123(2), pp. 207-218 (2005).
Bhaskar et al., "Synthesis, Antimicrobial and Antihyperlipidemic Activities of Some 4-Substituted-5,6,7,8-tetrhydrol [1]benzothieno[2,3-d]pyrimidines." Asian J Chemistry 2007, 19(7):5187-5194.

(Continued)

*Primary Examiner* — Wu-Cheng Winston Shen
*Assistant Examiner* — Christopher R Stone
(74) *Attorney, Agent, or Firm* — David W. Staple; Casimir Jones, S.C.

(57) ABSTRACT

The invention relates generally to effective treatment leukemia. In particular, the present invention provides compositions and methods to inhibit the interaction of menin with MLL and MLL-fusion oncoproteins, and well as systems and methods to screen for such compositions.

10 Claims, 15 Drawing Sheets

(56) References Cited

OTHER PUBLICATIONS

Sharma et al., "Synthesis of Thienopyrimidines and their Antipsychotic Activity." E Journal of Chemistry Jan. 2010, 7(2):655-664.

Kim et al, "Chemical Biology Investigation of Cell Death Pathways Activated by Endoplasmic Reticulum Stress Reveals Cytoprotective Modulators of ASK1." J Biological Chemistry Jan. 2009, 284(3):1593-1603.

Office Action dated Dec. 3, 2013, Chinese Application No. 201080050708.8, 15 pages.

SMR00018765, Pubchem, http://pubchem.ncbi.nlm.nih.gov/summary/summary.cgi?cid=1323703, 2007, 16 pages.

F1174-09147, Pubchem, http://pubchem.ncbi.nlm.nih.gov/summary/summary.cgi?cid=711090, 2007, 13 pages.

* cited by examiner

A)

B)

A)

B)

B)

A)

B)

A)

B)

C)

A)

B)

A)

B)

A)

B)

6G10: 2-[4-(4-Fluorophenyl)-1,3-Thiazol-2-Yl]Acetamide
4H8: 3-Pyridin-3-ylaniline
1F4: 5-methyl-2-phenyl-2H-1,2,3-triazole-4-carboxamide
4A6: 4-[4-(Hydroxymethyl)phenyl]pyridine

COMPOSITIONS AND METHODS FOR TREATMENT OF LEUKEMIA

The present application claims priority to U.S. Provisional Patent Application Ser. No. 61/240,102, filed Sep. 4, 2009, the entire disclosure of which is herein incorporated by reference in its entirety.

FIELD OF THE INVENTION

The invention relates generally to treatment of leukemia. In particular, the present invention provides compositions and methods to inhibit the interaction of menin with MLL and MLL-fusion oncoproteins, as well as systems and methods to screen for such compositions.

BACKGROUND OF THE INVENTION

Chromosomal translocations that affect the proto-oncogene Mixed Lineage Leukemia (MLL) occur in aggressive human acute leukemias, both in children and adults (Sorensen et al., J Clin Invest., 1994. 93(1): p. 429-37., Cox, et al., Am J Clin Pathol., 2004. 122(2): p. 298-306., herein incorporated by reference in their entireties). They are particularly common in infants with acute myeloblastic leukemia (AML) and acute lymphoblastic leukemia (ALL) and constitute up to 80% of all infant acute leukemia cases. Fusion of MLL with one of 60 partner genes forms a chimeric oncogene which upregulates HOX genes resulting in a blockage of blood cell differentiation that ultimately leads to acute leukemia (Eguchi et al. Int J. Hematol., 2003. 78(5): p. 390-401., herein incorporated by reference in its entirety). Patients with leukemias harboring MLL translocations have a very poor prognosis (35% five year survival) and it is clear that novel therapeutic strategies are urgently needed to treat these leukemias (Slany. Hematol Oncol., 2005. 23(1): p. 1-9., herein incorporated by reference in its entirety). Menin is a critical cofactor in MLL-associated leukemias. Menin is a tumor-suppressor protein encoded by the Multiple Endocrine Neoplasia (MEN) gene. Menin is a ubiquitously expressed nuclear protein that is engaged in interactions with a cohort of transcription factors, chromatin modifying proteins, and DNA processing and repair proteins (Agarwal et al. Horm Metab Res., 2005. 37(6): p. 369-74., herein incorporated by reference in its entirety). The biological function of menin remains unclear and is context dependent. It functions as a tumor suppressor in endocrine organs (Marx. Nat. Rev Cancer., 2005. 5(5): p. 367-75., herein incorporated by reference in its entirety) but has an oncogenic role in myeloid cells (Yokoyama et al., Cell., 2005. 123(2): p. 207-18., herein incorporated by reference in its entirety). Association of menin with oncogenic MLL fusion proteins constitutively up-regulates expression of HOX genes and impairs proliferation and differentiation of hematopoietic cells leading to leukemia development. Myeloid cells transformed with oncogenic MLL-AF9 fusion protein require menin for efficient proliferation (Chen et al., Proc Natl Acad Sci USA., 2006. 103(4): p. 1018-23., herein incorporated by reference in its entirety). Menin is also required to maintain oncogenic transformation induced by other MLL translocations, including MLL-ENL, MLL-GAS7 and MLL-AF6 (Yokoyama et al., Cell., 2005. 123(2): p. 207-18., herein incorporated by reference in its entirety), demonstrating that menin functions as a general oncogenic cofactor in MLL-related leukemias and implies the interaction of menin with MLL fusions is a valuable target for molecular therapy. The leukemogenic activity of MLL fusion oncoproteins is dependent on association with menin. Therefore, selective targeting of this interaction could provide an attractive therapeutic approach to develop novel drugs for the MLL-related leukemias.

SUMMARY OF THE INVENTION

In some embodiments, the present invention provides compositions for the treatment of leukemia which inhibit binding of one or more MLL fusion proteins to menin and/or MLL wild type to menin. In some embodiments, the composition comprises a thienopyrimidine class compound. In some embodiments, the thienopyrimidine class compound is of the general formula or pharmaceutically acceptable salts of thereof:

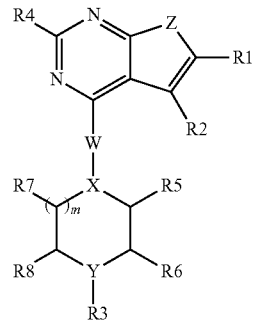

wherein R1, R2, R3, R4, R5, R6, R7, and R8 independently comprise: H, alkyl (e.g., methyl, ethyl, etc.) which might be further substituted or non-substituted, alkoxy further substituted or non-substituted, a halogen (e.g. F, Cl, Br, I, and At), a ketone, a carbocyclic ring, an aromatic ring, a heterocyclic aromatic ring comprising carbon and one or more nitrogen, oxygen and/or sulfur members which may be non-substituted or substituted with alkyl, aryl, halogen, hydrogen bond donor or acceptor, a heterocyclic non-aromatic ring comprising carbon and one or more nitrogen, oxygen and/or sulfur members which may be non-substituted or substituted with alkyl, aryl, halogen, hydrogen bond donor or acceptor, carbocyclic aromatic or non-aromatic ring attached or fused to the thienopyrimidine ring system non-substituted or substituted with alkyl, aryl, halogen, hydrogen bond donor or acceptor, carbocyclic or heterocyclic aromatic ring comprising carbon atoms and one or more nitrogen, oxygen and/or sulfur members fused to another aromatic ring, or a hydrogen bond donor or a hydrogen bond acceptor. Z is S or O or NH or CH—CH. W is present or absent and is NH or NH—$(CH_2)_n$ (n=0-10), or $(CH_2)_n$ (n=0-10) or O or O—$(CH_2)_n$ (n=0-10); X and Y are each independently N or C; m is 0-3 (where m=0, R7 is absent). In some embodiments, the present invention comprises any substituent that results in compounds inhibiting the interaction of menin with MLL and/or MLL fusion proteins that can be used to treat or prevent leukemia.

In some embodiments, the thienopyrimidine class compound is of the general formula or pharmaceutically acceptable salts of thereof:

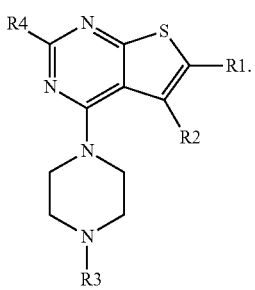

In some embodiments, the thienopyrimidine class compound has the structure:

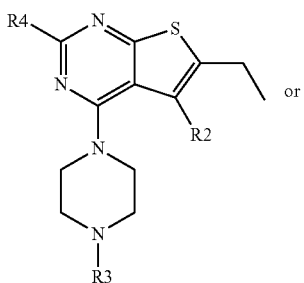

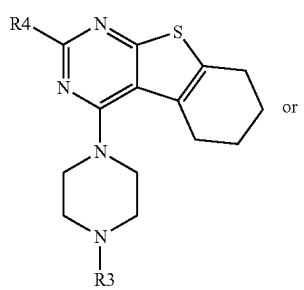

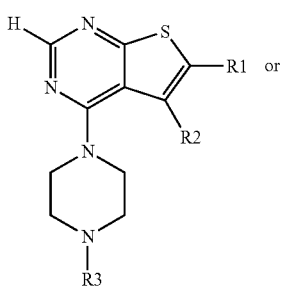

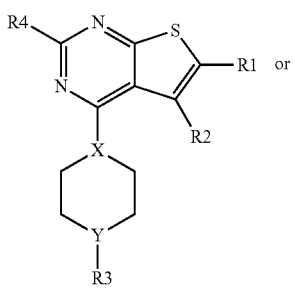

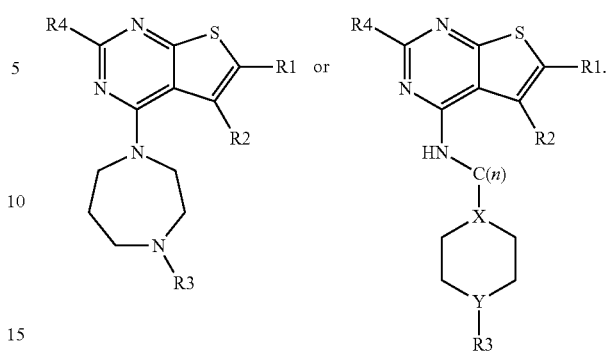

In some embodiments, the thienopyrimidine class compound is selected from Compounds 1-31 and 60-83.

In some embodiments, the composition comprises any structural analogues of compositions 1-31 and 60-83.

In some embodiments, the composition comprises a benzodiazepine class compound. In some embodiments, the benzodiazepine class compound is of the general formula or pharmaceutically acceptable salts of thereof:

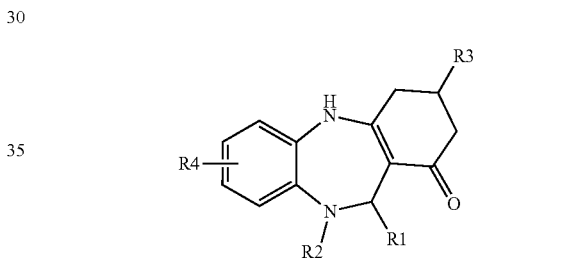

wherein R1, R2, R3, and R4 independently comprise: H, alkyl which might be substituted or non-substituted, acetyl, alkoxy, a halogen (e.g. F, Cl, Br, I, and At), a ketone, a carbocyclic ring, an aromatic ring, a heterocyclic aromatic ring comprising carbon and one or more nitrogen, oxygen and/or sulfur members which may be non-substituted or substituted with alkyl, aryl, halogen, hydrogen bond donor or acceptor, a heterocyclic non-aromatic ring comprising carbon and one or more nitrogen, oxygen and/or sulfur members which may be non-substituted or substituted with alkyl, aryl, halogen, hydrogen bond donor or acceptor, carbocyclic aromatic or non-aromatic ring fused or attached to the benzodiazepine ring system non-substituted or substituted with alkyl, aryl, halogen, hydrogen bond donor or acceptor, carbocyclic or heterocyclic aromatic ring comprising carbon atoms and one or more nitrogen, oxygen and/or sulfur members fused to another aromatic ring, or a hydrogen bond donor or a hydrogen bond acceptor. In some embodiments, the present invention comprises any substituent which result in compounds inhibiting the interaction of menin with MLL and/or MLL fusion proteins that can be used to treat or prevent leukemia.

In some embodiments, the benzodiazepine class compound has the structure:

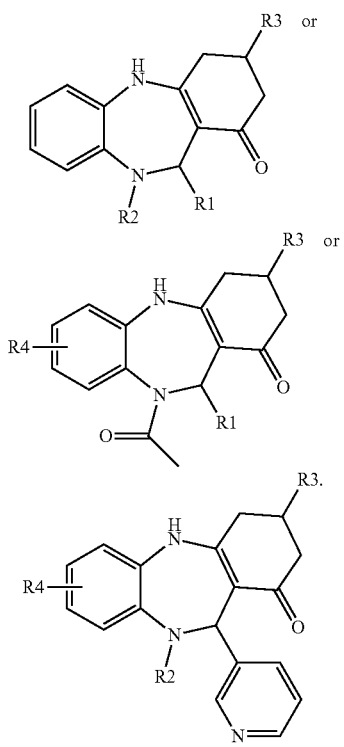

In some embodiments, the benzodiazepine class compound is selected from: Compounds 32-41 and 84-86.

In some embodiments, the compositions comprise structures of Compounds 42-59 or derivatives there.

In some embodiments, the compositions comprise any structural analogues of compositions 35-41 and 84-86.

The compositions may comprise combinations of any of the above compounds with one another or with other compounds of interest. Stereoisomers, salts, and derivates of the compounds are further contemplated.

In some embodiments, the present invention provides a method comprising: administering a composition for the treatment of leukemia (e.g., which inhibits binding of one or more MLL fusion proteins to menin or MLL wild type to menin) to a subject suffering from leukemia. In some embodiments, the leukemia comprises AML or ALL. In some embodiments, the composition comprises a thienopyrimidine class compound. In some embodiments, the composition comprises a benzodiazepine class compound. In some embodiments, the composition comprises compounds 42-59 and their analogues.

In some embodiments, the present invention provides a method of screening compounds effective in treating leukemia comprising assaying one or more compounds for inhibition of the interaction between MLL and menin. In some embodiments, the screening is performed in vitro. In some embodiments, the screening is performed in vivo. In some embodiments, the assaying comprises a fluorescence polarization assay. In some embodiments, the assaying comprises a time-resolved fluorescence resonance energy transfer assay. In some embodiments, the assaying comprises a nuclear magnetic resonance assay. In some embodiments, the assaying comprises cellular assays and mice studies.

In some embodiments, the present invention provides a method of inhibiting the interaction of MLL and menin comprising: (a) providing: (i) a sample comprising MLL and menin and (ii) a composition configured to inhibit the interaction of MLL and menin, (b) administering the composition to the sample, (c) contacting MLL and/or menin with the composition, and (d) inhibiting the interaction between MLL and menin, and between MLL fusion proteins and menin. In some embodiments, the sample comprises cells from a subject suffering from leukemia. In some embodiments, the subject is a human subject or a human patient. In some embodiments, the cells are within a subject suffering from leukemia. In some embodiments, the composition comprises a thienopyrimidine class compound. In some embodiments, the composition comprises a benzodiazepine class compound. In some embodiments, the composition comprises compounds 42-59 and their analogues.

In some embodiments, the present invention comprises any structural analogues of Compounds 1-86.

BRIEF DESCRIPTION OF THE DRAWINGS

The description provided herein is better understood when read in conjunction with the accompanying drawings which are included by way of example and not by way of limitation.

DEFINITIONS

Figure 1:
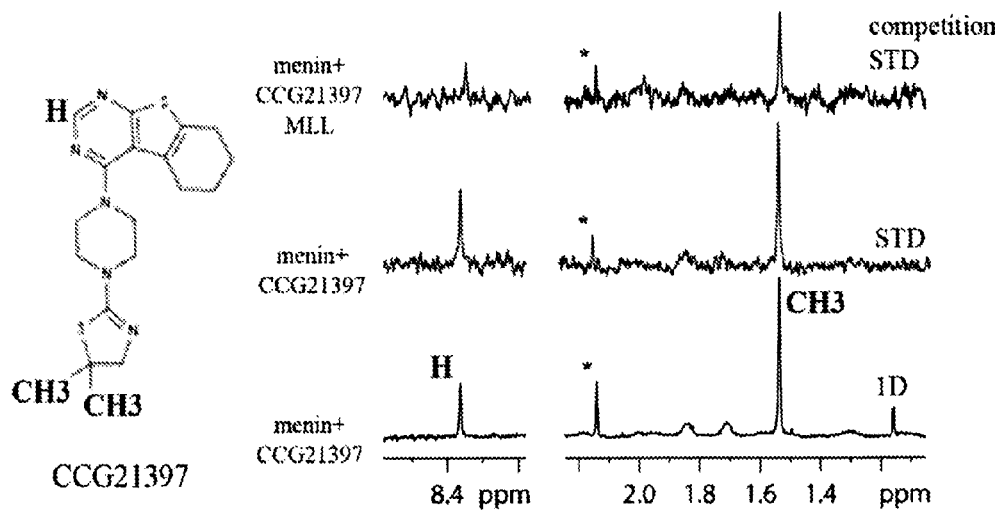
FIG. 1. A. Binding of Compound 1 (labeled as CCG21397; thienopyrimidine class) to menin demonstrated in STD (saturation transfer difference) experiment measured for 80 μM of Compound 1 and 2.5 μM menin: reference 1D spectrum (black) showing separately aromatic and aliphatic regions; STD spectrum (red) showing binding of Compound 1 to menin; competition STD spectrum (blue) showing the decrease of STD effect in the presence of 25 μM MLL peptide, which confirms specific binding of Compound 1 to menin. The H and $CH_3$ signals from the ligand shown on the spectra are labeled on the structure. B. Binding of Compound 33 (labeled as CCG23668; benzodiazepine class) to menin demonstrated in STD experiment measured for 100 μM Compound 33 and 2.5 μM menin: reference 1D spectrum (black) for the aliphatic region of the compound; STD spectrum (red) confirming binding to menin; competition STD spectrum (blue) showing the decrease of STD effect in the presence of 25 μM MLL peptide, which confirms specific binding of Compound 33 to menin. Signals from the ligand's methyl groups are labeled M1, M2 and M1', M2' (two sets of peaks are from different stereoisomers). The intensity of peak corresponding to impurity (labeled with asterix) is not affected by addition of MLL.
Figure 1:
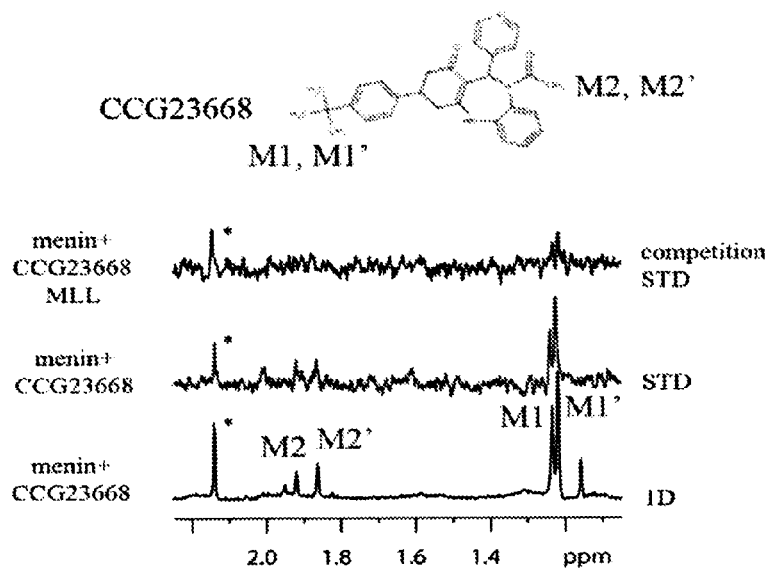

The term "system" refers a group of objects, compounds, methods, and/or devices that form a network for performing a desired objective.

As used herein a "sample" refers to anything capable of being subjected to the compositions and methods provided herein. The sample may be in vitro or in vivo. In some embodiments, samples are "mixture" samples, which samples from more than one subject or individual. In some embodiments, the methods provided herein comprise purifying or isolating the sample. In some embodiments, the sample is purified or unpurified protein. In some embodiments, a sample may be from a clinical or research setting. In some embodiments, a sample may comprise cells, fluids (e.g. blood, urine, cytoplasm, etc.), tissues, organs, lysed cells, whole organisms, etc. In some embodiments, a sample may be derived from a subject. In some embodiments, a sample may comprise one or more partial or whole subjects.

As used herein, the term "subject" refers to any animal including, but not limited to, insects, humans, non-human primates, vertebrates, bovines, equines, felines, canines, pigs, rodents (e.g., mice), and the like. The terms "subject" and "patient" may be used interchangeably, wherein the term "patient" generally refers to a subject seeking or receiving treatment or preventative measures from a clinician or health care provider. A subject may be of any stage of life (e.g. embryo, fetus, infant, neonatal, child, adult, live, dead, etc.).

As used herein, the term "subject at risk for cancer" refers to a subject with one or more risk factors for developing a specific cancer. Risk factors include, but are not limited to, gender, age, genetic predisposition, environmental exposure, and previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue or cells and the stage of the cancer. Cancers may be characterized by identifying cancer cells with the compositions and methods of the present invention.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention.

As used herein, the term "effective amount" refers to the amount of a compound (e.g., a compound having a structure presented above or elsewhere described herein) sufficient to effect beneficial or desired results. An effective amount can be administered in one or more administrations, applications or dosages and is not limited to or intended to be limited to a particular formulation or administration route.

As used herein, the term "co-administration" refers to the administration of at least two agent(s) (e.g., a compound having a structure presented above or elsewhere described herein) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "instructions for administering said compound to a subject," and grammatical equivalents thereof, includes instructions for using the compositions contained in a kit for the treatment of conditions characterized by viral infection (e.g., providing dosing, route of administration, decision trees for treating physicians for correlating patient-specific characteristics with therapeutic courses of action). The compounds of the present invention (e.g. as shown in structures above and elsewhere presented herein) can be packaged into a kit, which may include instructions for administering the compounds to a subject.

DETAILED DESCRIPTION

In some embodiments, the present invention provides compositions and methods for prevention and/or treatment of leukemia (e.g. MLL-related leukemia and other acute leukemias). In some embodiments, the present invention provides compositions and method for the inhibition of the protein-protein interaction between menin and MLL fusion proteins and/or menin and MLL wild type protein. In some embodiments, compositions and methods inhibit the interaction that is important for the oncogenic (e.g. leukemogenic) potential of MLL fusions. In some embodiments, the present invention provides small molecule inhibitors of interactions between menin and MLL fusion proteins and/or menin and MLL wild type protein. In some embodiments, compositions and methods reverse (e.g. inhibit, decrease, abolish, etc.) the oncogenic (e.g. leukemogenic) potential of MLL fusions. In some embodiments, compositions find utility in targeted therapies (e.g. anti-leukemia agents). In some embodiments, compounds block menin-MLL interactions.

In some embodiments, the present invention provides compositions which inhibit the interaction between MLL (e.g. MLL fusion proteins and MLL wild type) and menin. In same embodiments, any compounds, small molecules (e.g. pharmaceuticals, drugs, drug-like molecules, etc.), macromolecules (e.g. peptides, nucleic acids, etc.) and/or macromolecular complexes which inhibit the MLL-menin interaction find utility in the present invention. In some embodiments, the present invention provides small molecule compounds which inhibit MLL-menin interactions. In some embodiments, compositions of the present invention decrease the affinity of menin for MLL (e.g. MLL fusion proteins) and/or MLL (e.g. MLL wild type protein) for menin. In some embodiments, compositions of the present invention disrupt bonding (e.g. hydrogen bonding, ionic bonding, covalent bonding, etc.), molecular interactions (e.g. hydrophobic interactions, electrostatic interactions, van der Waals interactions, etc.), shape recognition, and/or molecular recognition between MLL (e.g. MLL fusion proteins or MLL wild type protein) and menin. However, an understanding of the mechanisms of action is not required to practice the invention and the invention is not limited to any particular mechanism of action.

The present invention provides any small molecules or classes of small molecules which disrupt, target, or inhibit MLL/menin interactions; and/or treat/prevent leukemia. In some embodiments, small molecules are effective in inhibiting the interaction of MLL-fusion proteins with menin or MLL wild type protein with menin. In particular embodiments, the present invention provides thienopyrimidine and benzodiazepine classes of small molecules. In some embodiments, thienopyrimidine and benzodiazepine small molecules inhibit the interaction of MLL (e.g. MLL-fusion proteins or MLL wild type) with menin. In some embodiments, thienopyrimidine and benzodiazepine small molecules inhibit the oncogenic (e.g. leukemogenic) effects of MLL-fusion proteins, and/or MLL-menin and MLL fusion protein-menin interactions. In some embodiments, thienopyrimidine and benzodiazepine small molecules treat and/or prevent leukemia (e.g. MLL-dependant leukemias, MLL-related leukemias, or other leukemias with and without high level of Hox gene expression etc.).

In some embodiments, thienopyrimidine class small molecules are of the general, structures:

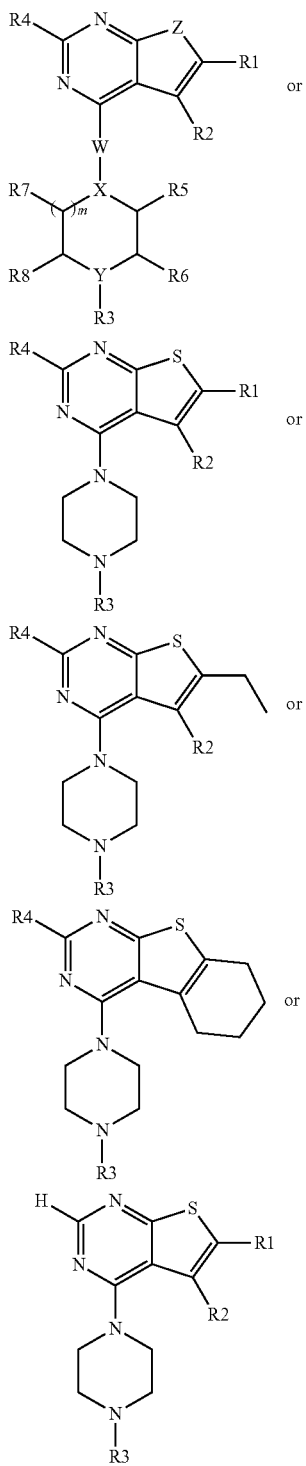

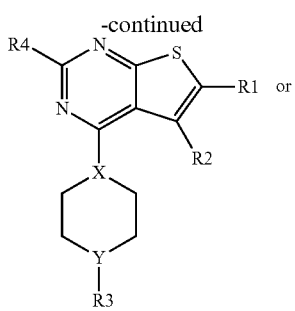

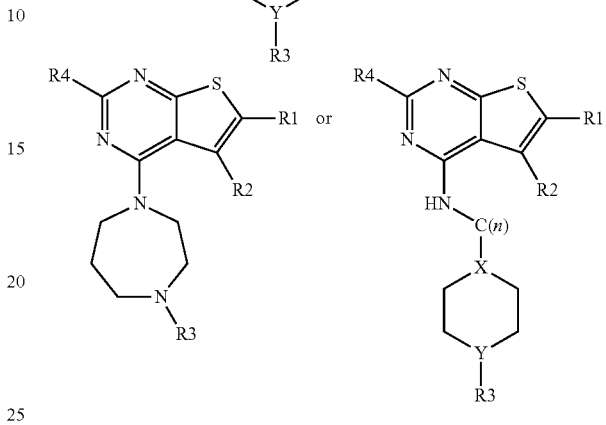

or pharmaceutically acceptable salts or hydrates thereof, wherein: R1, R2=H, alkyl which might be substituted or non-substituted, alkoxy further substituted or non-substituted, a halogen (e.g. F, Cl, Br, I, and At), a carbocyclic aromatic ring, a carbocyclic aromatic ring comprising six carbons, a carbocyclic non-aromatic ring, a carbocyclic non-aromatic ring of three to six carbons, a heterocyclic aromatic ring, a five or six member heterocyclic aromatic ring comprising carbon atoms and one or more nitrogen, oxygen and/or sulfur members, any aromatic or non-aromatic ring non-substituted or substituted with alkyl, aryl, halogen, hydrogen bond donor or acceptor, a five or six member heterocyclic non-aromatic ring comprising carbon atoms and one or more nitrogen, oxygen and/or sulfur members, a carbocyclic aromatic or non-aromatic ring fused to the thienopyrimidine ring system, a five or six member carbocyclic aromatic or non-aromatic ring fused to the thienopyrimidine ring system, any aromatic or non-aromatic ring system non-substituted or substituted with alkyl, halogen, hydrogen bond donor or acceptor fused to thienopyrimidine ring system, a five or six member carbocyclic or heterocyclic aromatic ring comprising carbon atoms and one or more nitrogen, oxygen and/or sulfur members fused to another aromatic ring substituted or non-substituted, or a hydrogen bond donor or a hydrogen bond acceptor; in some embodiments R1 and R2 are covalently bound to one another (e.g., exist within a ring); R3, R4, R5, R6, R7, and R8=H, alkyl substituted or non-substituted, alkoxy, a halogen (e.g. F, Cl, Br, I, and At), a carbocyclic aromatic ring comprising six carbons, a carbocyclic non-aromatic ring of three to six carbons, a five or six member heterocyclic aromatic ring comprising carbon atoms and one or more nitrogen, oxygen and/or sulfur members, a five or six member heterocyclic non-aromatic ring comprising carbon atoms and one or more nitrogen, oxygen and/or sulfur members, any aromatic or non-aromatic ring non-substituted or substituted with alkyl, aryl, halogen, hydrogen bond donor or acceptor, a five or six member carbocyclic or heterocyclic aromatic ring comprising carbon atoms and one or more nitrogen, oxygen and/or sulfur members fused to another aromatic ring, a hydrogen bond donor or a hydrogen bond acceptor, etc. Z is S or O or NH or CH—CH. W is present or absent and is NH or NH—

(CH$_2$)$_n$ (n=0-10), or (CH$_2$)$_n$ (n=0-10) or O or O—(CH$_2$)$_n$ (n=0-10); X and Y are each independently N or C; m is 0-3 (where m=0, R7 is absent). In some embodiments, R1, R2, R3, and R4 comprise any substituents which result in compounds which inhibit the interaction of MLL-fusion proteins with menin and/or treat or prevent leukemia.

In some embodiments, thienopyrimidine class small molecules comprise the compositions of Tables 1 and 2, derivatives, combinations, pharmaceutically acceptable salts, and/or hydrates thereof. In some embodiments, thienopyrimidine class small molecules inhibit the interaction of MLL (e.g. MLL fusion proteins) with menin. In some embodiments, thienopyrimidine class small molecules reverse and/or inhibit the oncogenic (e.g. leukemogenic) effects of MLL-fusion proteins, and/or MLL/menin and MLL fusion proteins/menin interactions. In some embodiments, thienopyrimidine class small molecules prevent or treat leukemia.

In some embodiments, benzodiazepine class small molecules are of the general structure:

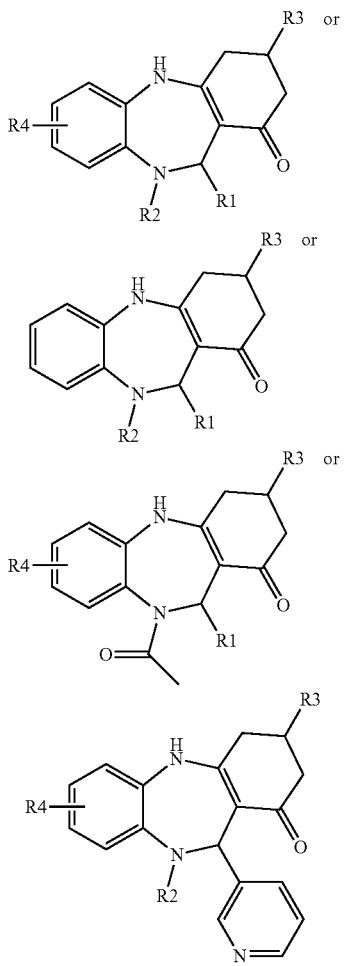

or pharmaceutically acceptable salt or hydrate thereof, wherein: R1, R2, R3, R4=H, alkyl, acetyl, alkoxy, ketone, a halogen (e.g. F, Cl, Br, I, and At), a carbocyclic aromatic ring, a carbocyclic aromatic ring comprising six carbons, a carbocyclic non-aromatic ring, a carbocyclic non-aromatic ring of three to six carbons, a heterocyclic aromatic ring, a five or six member heterocyclic aromatic ring comprising carbon atoms and one or more nitrogen, oxygen and/or sulfur members, a heterocyclic non-aromatic ring, a five or six member heterocyclic non-aromatic ring comprising carbon atoms and one or more nitrogen, oxygen and/or sulfur members, a five or six member carbocyclic or heterocyclic aromatic ring comprising carbon atoms and one or more nitrogen, oxygen and/or sulfur members fused to alkyl, alkoxy, halogen (e.g. F, Cl, Br, I, and At), a hydrogen bond donor, a hydrogen bond acceptor or to another aromatic or non-aromatic ring, a five or six member heterocyclic non-aromatic ring comprising carbon atoms and one or more nitrogen, oxygen and/or sulfur members fused to another aromatic ring, a hydrogen bond donor or a hydrogen bond acceptor, etc. In some embodiments, R1, R2, R3, and R4 comprise any substituents which result in compounds which inhibit the interaction of MLL-fusion proteins with menin and/or treat or prevent leukemia.

In some embodiments, benzodiazepine class small molecules comprise the compositions of Table 3, derivatives, combinations, pharmaceutically acceptable salts, and/or hydrates thereof. In some embodiments, benzodiazepine class small molecules inhibit the interaction of MLL (e.g. MLL fusion proteins or MLL wild type) with menin. In some embodiments, benzodiazepine class small molecules reverse and/or inhibit the oncogenic (e.g. leukemogenic) effects of MLL, MLL-fusion proteins, and/or MLL/menin interactions. In some embodiments, benzodiazepine class small molecules prevent or treat leukemia.

In some embodiments, the compound has the structure of Compounds 42-59, or derivatives thereof.

In some embodiments, the present invention provides administration of compositions of the present invention to subjects (e.g. leukemia patients) to treat or prevent disease (e.g. cancer, leukemia, MLL-related leukemia, etc.). In some embodiments, the present invention provides administration of compositions for the treatment or prevention of leukemia (e.g. acute leukemias, chronic leukemias, lymphoblastic leukemias, lymphocytic leukemias, myeloid leukemias, myelogenous leukemias, Acute lymphoblastic leukemia (ALL), Chronic lymphocytic leukemia (CLL), Acute myelogenous leukemia (AML), Chronic myelogenous leukemia (CML), Hairy cell leukemia (HCL), T-cell prolymphocytic leukemia (T-PLL), Large granular lymphocytic leukemia, MLL-positive leukemias, MLL-induced lukemias, etc.).

In some embodiments, any of the above compounds is co-administered or used in combination with a known therapeutic agent (e.g., methotrexate, 6-mercaptopurine, antibody therapies, etc.).

In some embodiments, the compositions of the present invention are provided as pharmaceutical and/or therapeutic compositions. The pharmaceutical and/or therapeutic compositions of the present invention can be administered in a number of ways depending upon whether local or systemic treatment is desired and upon the area to be treated. Administration can be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Compositions and formulations for topical administration can include transdermal patches, ointments, lotions, creams, gels, drops, suppositories, sprays, liquids and powders. Conventional carriers; aqueous, powder, or oily bases; thickeners; and the like can be necessary or desirable. Compositions and formulations for oral administration include powders or granules, suspensions or solutions in water or non aqueous media, capsules, sachets or tablets. Thickeners, flavoring agents, diluents, emulsifiers, dispersing aids or binders can be desirable. Compositions and formulations for parenteral, intrathecal or intraventricular administration can include sterile aqueous solutions that can also contain buffers, diluents and other suitable additives such as, but not limited to, penetration enhancers, carrier compounds and other pharmaceutically acceptable carriers or excipients. Pharmaceutical and/or therapeutic compositions of the present invention include, but are not limited to, solutions, emulsions, and liposome containing formulations. These compositions can be generated from a variety of components that include, but are not limited to, preformed liquids, self emulsifying solids and self emulsifying semisolids.

The pharmaceutical and/or therapeutic formulations of the present invention, which can conveniently be presented in unit dosage form, can be prepared according to conventional techniques well known in the pharmaceutical/nutriceutical industries. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product. The compositions of the present invention can be formulated into any of many possible dosage forms such as, but not limited to, tablets, capsules, liquid syrups, soft gels, suppositories, and enemas. The compositions of the present invention can also be formulated as suspensions in aqueous, non aqueous, oil-based, or mixed media. Suspensions can further contain substances that increase the viscosity of the suspension including, for example, sodium carboxymethylcellulose, sorbitol and/or dextran. The suspension can also contain stabilizers. In one embodiment of the present invention the pharmaceutical compositions can be formulated and used as foams. Pharmaceutical foams include formulations such as, but not limited to, emulsions, microemulsions, creams, jellies and liposomes. While basically similar in nature these formulations vary in the components and the consistency of the final product.

Dosing and administration regimes are tailored by the clinician, or others skilled in the pharmacological arts, based upon well known pharmacological and therapeutic considerations including, but not limited to, the desired level of therapeutic effect, and the practical level of therapeutic effect obtainable. Generally, it is advisable to follow well-known pharmacological principles for administrating chemotherapeutic agents (e.g., it is generally advisable to not change dosages by more than 50% at time and no more than every 3-4 agent half-lives). For compositions that have relatively little or no dose-related toxicity considerations, and where maximum efficacy is desired, doses in excess of the average required dose are not uncommon. This approach to dosing is commonly referred to as the "maximal dose" strategy. In certain embodiments, the compounds are administered to a subject at a dose of about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone. Dosing may be once per day or multiple times per day for one or more consecutive days.

EXPERIMENTAL

Compounds 1-3 and 5-8 are commercially available from Chembridge Corporation. Compound 9 is commercially available from Asinex. Compound 10 is commercially available from InterbioScreen Ltd., Compounds 11 and 32-41 are commercially available from Chemdiv Inc. Compounds 12-27 and 31 are commercially available from Enamine. Compound 4 is commercially available from Labotest (LT00160569). Compounds 28-30 are commercially available from Princeton Biomolecular Research. Remaining compounds were obtained from commercially available sources as indicated below, or were synthesized. The following compounds were used as HCl salts: Compounds 2, 4, 6-8, 26, 27, 64-72, and 75-76.

EXAMPLE 1

Compound Screening

Fluorescence Polarization Assay. Assays effective in monitoring the inhibition of the MLL binding to menin were developed during experiments performed during the development of embodiments of the present invention. A fluorescein-labeled 12-amino acid peptide derived from MLL containing the high affinity menin binding motif was produced (Yokoyama et al., Cell., 2005. 123(2): p. 207-18., herein incorporated by reference in its entirety). Upon binding of the peptide (1.7 kDa) to the much larger menin (~67 kDa), the rotational correlation time of the fluorophore (peptide labeled with fluorescein at N-terminus) changes significantly, resulting in a substantial increase in the measured fluorescence polarization and fluorescence anisotropy (excitation at 500 nm, emission at 525 nm). The fluorescence polarization (FP) assay was utilized to determine the $K_d$ for the binding of menin and the MLL peptide using a serial dilution of menin and 50 nM fluorescein-labeled MLL peptide. The titration curve demonstrates nanomolar affinity ($K_a$=56 nM) for the menin-MLL interaction.

The effectiveness of compounds ($IC_{50}$ values) in inhibiting the menin-MLL interaction was determined in the FP competition experiments. Compounds that inhibit the interaction decrease the fluorescence anisotropy which is being used as a read-out for compound screening and for $IC_{50}$ determination: For validation of the FP assay, a control competition experiment with unlabeled MLL peptide (no fluorescein attached) was performed. The competitive displacement of the fluorescein-labeled MLL peptide from menin by unlabeled MLL peptide was monitored. Using this assay, the $IC_{50}$ value for the MLL peptide with menin: $IC_{50}$=0.23 μM. In some embodiments of the present invention, the same competition FP assay is used for screening compounds targeting menin and inhibiting the menin-MLL interaction.

HTRF assay. One potential limitation of the above FP assay is the risk of selection of compounds that may interfere with the FP assays and produce so called "false-positives". Therefore, during development of embodiments of the present invention, a time-resolved fluorescence resonance energy transfer (TR-FRET) assay was utilized as a secondary, assay (e.g. for confirmation of results), commercialized by CISBIO as homogeneous time-resolve fluorescence (HTRF) assay. In some embodiments, the HTRF assay may be the primary assay and the FP assay is used as a secondary assay to confirm results. HTRF is based on the non-radiative energy transfer of the long-lived emission from the Europium cryptate ($Eu^{3+}$-cryptate) donor to the allophycocyanin (XL665) acceptor, combined with time-resolved detection. When these two fluorophores are brought together by a biomolecular interaction, a portion of the energy captured by the $Eu^{3+}$-cryptate during excitation at 337 nm is released through fluorescence emission of donor at 620 nm, while remaining energy is transferred to XL665 acceptor and released as specific fluorescence at 665 nm. In the HTRF used in the present invention, and development of embodiments thereof, $Eu^{3+}$-cryptate-donor is conjugated with mouse anti-6His monoclonal antibody which binds His-tagged menin, and XL665-acceptor is conjugated to streptavidin (SA-XL665) which binds biotinylated MLL peptide. The interaction of menin with the MLL peptide brings together donor and acceptor resulting in energy transfer to acceptor reflected by the increased fluorescence emission at 665 nm and increased HTRF ratio (emission intensity at 665 nm/emission intensity at 620 nm). Inhibition of the menin-MLL interaction by a competitor separates donor from acceptor, resulting in decreased emission at 665 nm and decreased HTRF ratio. The assay was validated by running the titration experiment with unlabeled MLL peptide, which resulted in $IC_{50}$=2.3 µM, remaining in a good agreement with the FP data.

NMR spectroscopy validation of lead compounds. In embodiments of the present invention, and during development thereof, NMR spectroscopy: saturation transfer difference (STD), competition STD, and WaterLOGSY experiments to validate binding of compounds to menin. STD provides a reliable method, based on principles vastly different form fluorescence that is commonly used for drug screening (e.g. by pharmaceutical companies). The principle of the STD experiment is based on the transfer of magnetization from a protein to a small molecule. Such a transfer occurs only when the ligand-protein contact is direct, and can be detected when the ligand is in fast exchange between bound and unbound state (Mayer & Meyer. J Am Chem Soc., 2001. 123(25): p. 6108-17., herein incorporated by reference in its entirety). The difference spectrum of the ligand recorded with and without protein saturation is analyzed. To detect binding of compounds to menin the STD spectra of compounds in the presence of 2.5 µM of menin are measured. The sensitivity of the experiment is high due to the significant size of menin (~70 kDa).

Library Screening. During development of embodiments of the present invention, high through-put screening (HTS) of 65,000 compounds tested at 20 µM has been carried out to identify compounds targeting the menin-MLL interaction. Primary screening was performed using FP. About 1400 compounds demonstrated inhibition in primary screening, out of which 240 re-confirmed. 180 compounds with no significant interference with FP (as confirmed in a non-FP assay) were selected for dose response curves (DRC), which was carried out by two independent FP assays: FLSN_MLL and Texas Red_MLL as fluorophores (TR_MLL was used to exclude "false positives" interfering with fluorescein). DRC demonstrated 40 compounds which were active in both FP assays. After detailed analysis, 16 compounds were selected for further analysis. The compounds were tested using FP with both fluorophores and HTRF, resulting in 5 compounds with $IC_{50}$ values below 100 µM. The most potent compound, Compound 1, had an $IC_{50}$ value of 1.9 uM. The most potent compounds can be clustered into two structural groups, indicating two classes (thienopyrimidine class and benzodiazepine class). Compounds from each cluster were tested by NMR, confirming they do bind to menin and compete with MLL for binding, which indicates their utility as anti-leukemia agents.

EXAMPLE 2

Elaboration of Thienopyrimidine Class of Compounds

Compound 1 was the most effecting inhibitory compound to arise out of screening performed during development of embodiments of the present invention. Compound 1, obtained from independent commercial suppliers, was re-tested by FP and HTRF for its inhibition of the menin-MLL interaction and obtained an identical $IC_{50}$ of 1.9 µM (Table 1). Two structurally related compounds were also identified in the same screening (Compound 2 and Compound 3, Table 1). In addition, 41 analogues of Compound 1 were purchased from commercial suppliers and 1.0 analogues were synthesized and tested for their inhibition of the menin-MLL interaction in FP assay resulting in a number of active compounds (Tables 1 and 2). Compound 4 demonstrates in vitro $IC_{50}$ comparable to the parent compound, but improved solubility, making it more suitable for cellular studies. Compound 1 was converted to HCl salt resulting in Compound 64 which improved its solubility. Synthesized compounds: 65, 66, 67, 70 showed more potent activity in in vitro FP assay (Table 2), with the most potent Compound 70 ($IC_{50}$=0.43 µM). Tables 1 and 2 list $IC_{50}$ data for a number of active compounds from the thienopyrimidine class.

TABLE 1

Structures and activities for thienopyrimidine class of compounds measured by FP and HTRF.

| Compound | Structure | $IC_{50}$ in FP assay with FLSN-MLL (µM) | $IC_{50}$ in HTRF assay (µM) |
|---|---|---|---|
| Compound 1 | 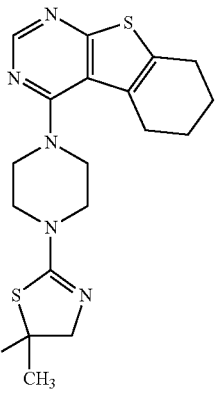 | 1.9 | 1.2 |

TABLE 1-continued
Structures and activities for thienopyrimidine class of compounds measured by FP and HTRF.
| Compound | Structure | IC$_{50}$ in FP assay with FLSN-MLL (μM) | IC$_{50}$ in HTRF assay (μM) |
| --- | --- | --- | --- |
| Compound 2 | 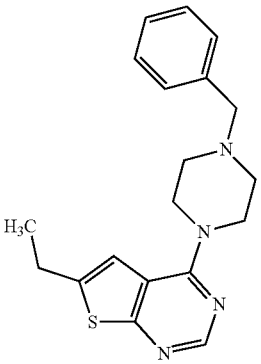 [SMILES: CCc1cc2c(N3CCN(Cc4ccccc4)CC3)ncnc2s1] | 42 | 85 |
| Compound 3 | 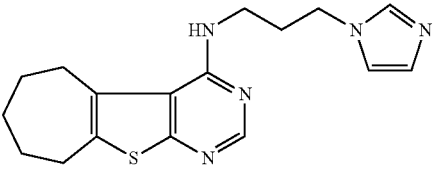 [SMILES: c1cn(CCCNc2ncnc3sc4c(c23)CCCCC4)cn1] | 83 | 35 |
| Compound 5 | 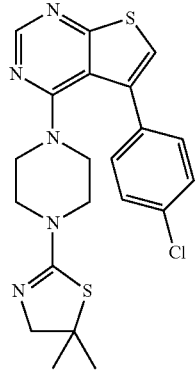 [SMILES: CC1(C)CN=C(N2CCN(c3ncnc4scc(-c5ccc(Cl)cc5)c34)CC2)S1] | NS, delta at 150 μM = 12% | |
| Compound 6 | 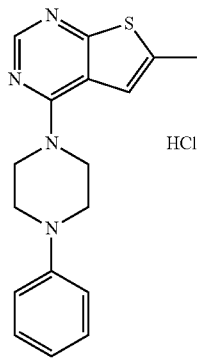 [SMILES: Cc1cc2c(N3CCN(c4ccccc4)CC3)ncnc2s1 ; Cl] | NA | |

TABLE 1-continued
Structures and activities for thienopyrimidine class of compounds measured by FP and HTRF.
| Compound | Structure | IC$_{50}$ in FP assay with FLSN-MLL (μM) | IC$_{50}$ in HTRF assay (μM) |
|---|---|---|---|
| Compound 7 | 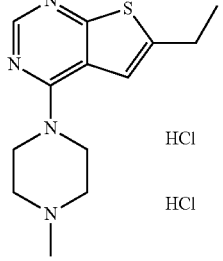 | 170 | |
| Compound 8 | 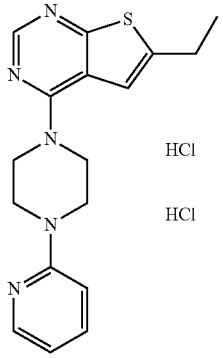 [SMILES: CCc1cc2c(N3CCN(c4ccccn4)CC3)ncnc2s1 ; Cl ; Cl] | 60 | |
| Compound 9 | 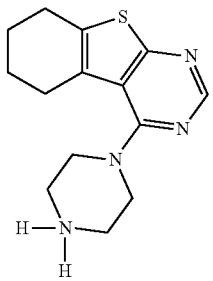 | 540 | |
| Compound 10 | 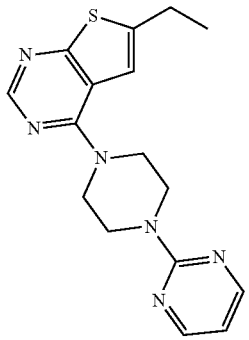 [SMILES: CCc1cc2c(N3CCN(c4ncccn4)CC3)ncnc2s1] | 250 | |

TABLE 1-continued
Structures and activities for thienopyrimidine class of compounds measured by FP and HTRF.
| Compound | Structure | IC$_{50}$ in FP assay with FLSN-MLL (μM) | IC$_{50}$ in HTRF assay (μM) |
|---|---|---|---|
| Compound 11 | 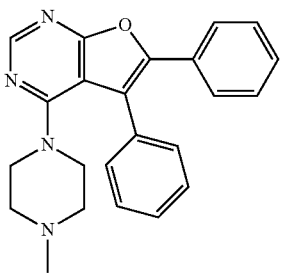 [SMILES: CN1CCN(c2ncnc3oc(-c4ccccc4)c(-c4ccccc4)c23)CC1] | 500 | |
| Compound 12 | 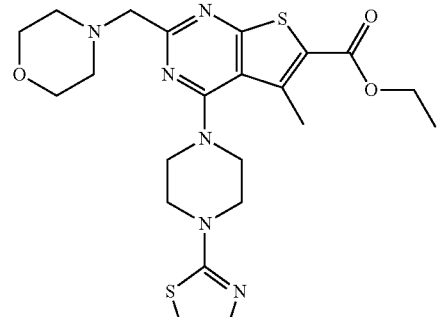 | NA up to 100 μM | |
| Compound 13 | 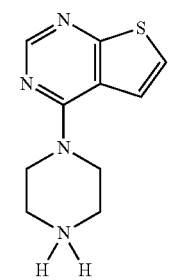 | NS, delta at 1 mM = 20% | |
| Compound 14 | 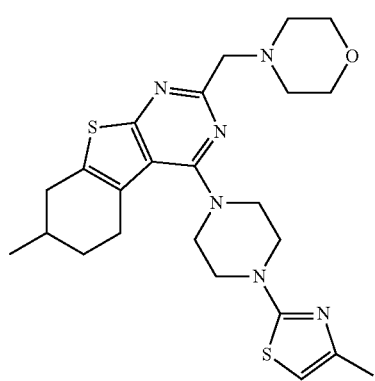 | 250 | |

TABLE 1-continued
Structures and activities for thienopyrimidine class of compounds measured by FP and HTRF.
| Compound | Structure | IC$_{50}$ in FP assay with FLSN-MLL (μM) | IC$_{50}$ in HTRF assay (μM) |
|---|---|---|---|
| Compound 15 | 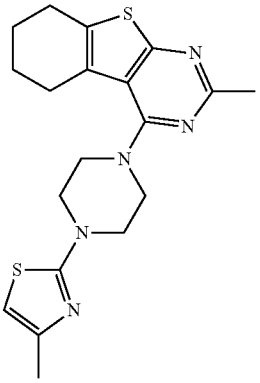 [SMILES: Cc1csc(N2CCN(c3nc(C)nc4sc5c(c34)CCCC5)CC2)n1] |  | 49 |
| Compound 16 | 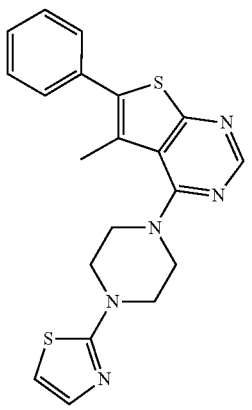 [SMILES: Cc1c(-c2ccccc2)sc2ncnc(N3CCN(c4nccs4)CC3)c12] |  | 71 |
| Compound 17 | 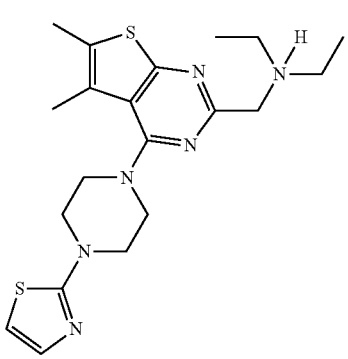 |  | NA up to 250 uM |
| Compound 18 | 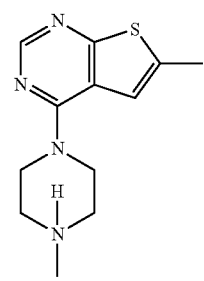 |  | NS, delta at 500 uM = 35% |

TABLE 1-continued
Structures and activities for thienopyrimidine class of compounds measured by FP and HTRF.
| Compound | Structure | IC$_{50}$ in FP assay with FLSN-MLL (μM) | IC$_{50}$ in HTRF assay (μM) |
| --- | --- | --- | --- |
| Compound 19 | 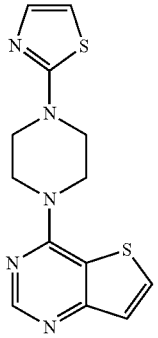 [SMILES: c1csc(N2CCN(c3ncnc4ccsc34)CC2)n1] | | NS, delta at 1 mM = 40% |
| Compound 20 | 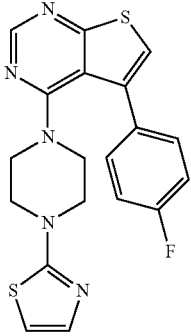 [SMILES: Fc1ccc(-c2csc3ncnc(N4CCN(c5nccs5)CC4)c23)cc1] | | 125 |
| Compound 21 | 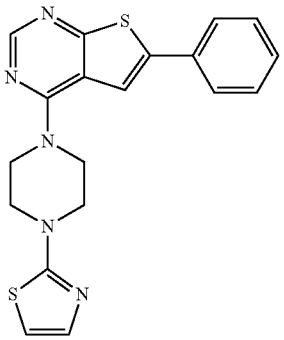 [SMILES: c1ccc(-c2cc3c(N4CCN(c5nccs5)CC4)ncnc3s2)cc1] | | 50 |
| Compound 22 | 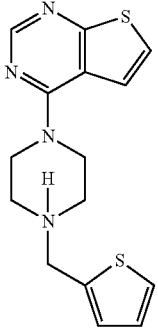 | | NS, delta at 500 μM = 20% |

TABLE 1-continued

Structures and activities for thienopyrimidine class of compounds measured by FP and HTRF.

| Compound | Structure | IC$_{50}$ in FP assay with FLSN-MLL (μM) | IC$_{50}$ in HTRF assay (μM) |
| --- | --- | --- | --- |
| Compound 23 | thienopyrimidine-piperazine-phenyl | | NS, delta at 250 μM = 20% |
| Compound 24 | thienopyrimidine-piperazine-pyrimidine | | NA up to 1 mM |
| Compound 25 | thienopyrimidine-piperazine-(NH-pyridine) | | NS, delta at 1 mM = 40% |
| Compound 26 | thienopyrimidine-piperazine-NH-methyl | | NS, delta at 1 mM = 15% |

TABLE 1-continued

Structures and activities for thienopyrimidine class of compounds measured by FP and HTRF.

| Compound | Structure | IC$_{50}$ in FP assay with FLSN-MLL (μM) | IC$_{50}$ in HTRF assay (μM) |
| --- | --- | --- | --- |
| Compound 27 | 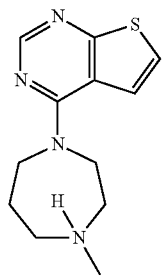 | 350 | |
| Compound 4 | 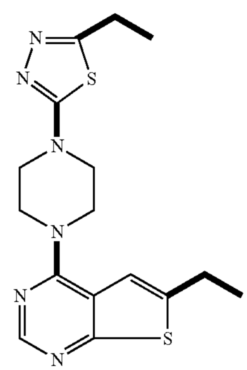 | 3.8 | |
| Compound 28 | 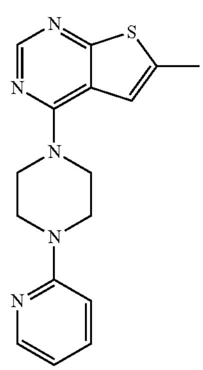 [SMILES: Cc1cc2c(N3CCN(c4ccccn4)CC3)ncnc2s1] | NS, delta at 0.5 mM = 30% | |
| Compound 29 | 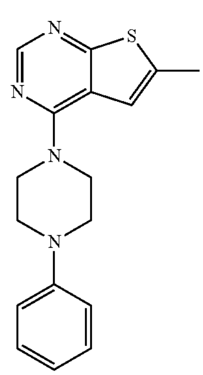 [SMILES: Cc1cc2c(N3CCN(c4ccccc4)CC3)ncnc2s1] | NA up to 250 μM | |

TABLE 1-continued

Structures and activities for thienopyrimidine class of compounds measured by FP and HTRF.

| Compound | Structure | $IC_{50}$ in FP assay with FLSN-MLL (μM) | $IC_{50}$ in HTRF assay (μM) |
|---|---|---|---|
| Compound 30 | 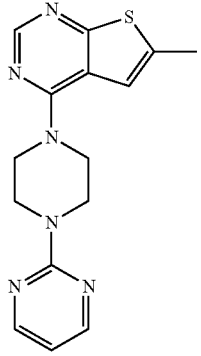 | NS, delta at 0.5 mM = 17% | |
| Compound 31 | 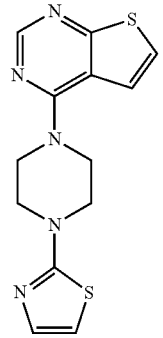 [SMILES: c1csc(N2CCN(c3ncnc4sccc34)CC2)n1] | 29.5 | |

NA—no activity,

NS—no saturation on titration curve.

$IC_{50}$ values < 100 μM are in bold.

TABLE 2

Structures and activities for thienopyrimidine class of compounds.

| ID | Structure | $IC_{50}$ (μM) | Vendor cat # |
|---|---|---|---|
| Compound 60 | 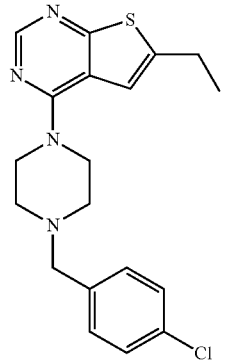 [SMILES: CCc1cc2c(N3CCN(Cc4ccc(Cl)cc4)CC3)ncnc2s1] | 30 | PrincetonBio OSSK_851527 |

TABLE 2-continued
Structures and activities for thienopyrimidine class of compounds.
| ID | Structure | IC$_{50}$ (μM) | Vendor cat # |
|---|---|---|---|
| Compound 61 | 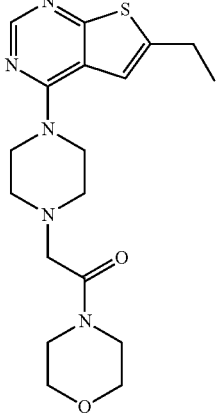 | 20 | Enamine T6333361 |
| Compound 62 | 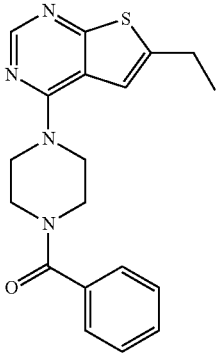 [SMILES: CCc1cc2c(N3CCN(C(=O)c4ccccc4)CC3)ncnc2s1] | 10 | ChemBridge 5728395 |
| Compound 63 | 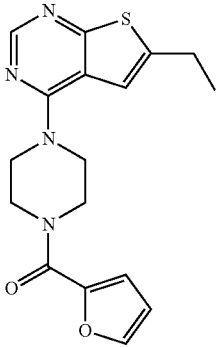 [SMILES: CCc1cc2c(N3CCN(C(=O)c4ccco4)CC3)ncnc2s1] | 12 | Asinex BAS 00933720 |
| Compound 64 Compound 1 converted to HCl salt | 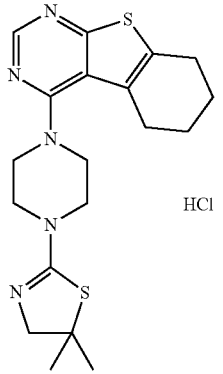 [SMILES: CC1(C)CN=C(N2CCN(c3ncnc4sc5c(c34)CCCC5)CC2)S1 ; Cl] | 1.9 | Labotest LT01870086 |

TABLE 2-continued
Structures and activities for thienopyrimidine class of compounds.
| ID | Structure | IC$_{50}$ (µM) | Vendor cat # |
|---|---|---|---|
| Compound 65 | 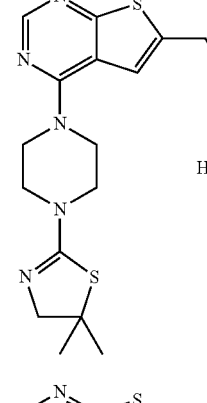 | 1.2 | synthesized |
| Compound 66 | 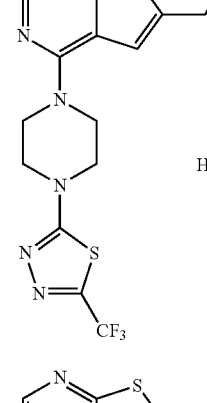 | 1.1 | synthesized |
| Compound 67 | 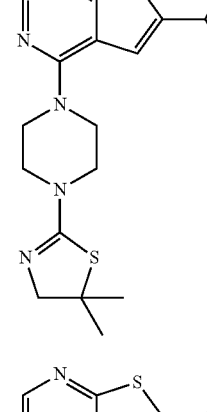 | 0.65 | synthesized |
| Compound 68 | 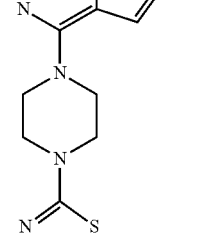 | 2.4 | synthesized |

TABLE 2-continued
Structures and activities for thienopyrimidine class of compounds.
| ID | Structure | IC$_{50}$ (μM) | Vendor cat # |
|---|---|---|---|
| Compound 69 | 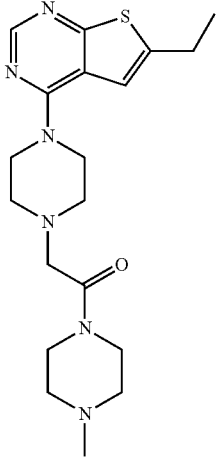 [SMILES: CCc1cc2c(N3CCN(CC(=O)N4CCN(C)CC4)CC3)ncnc2s1] | 16 | synthesized |
| Compound 70 | 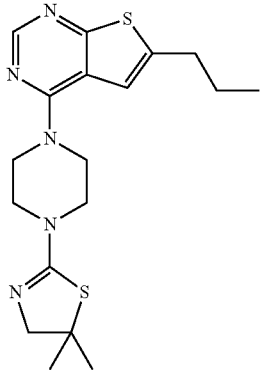 [SMILES: CCCc1cc2c(N3CCN(C4=NCC(C)(C)S4)CC3)ncnc2s1] | 0.43 | synthesized |
| Compound 71 | 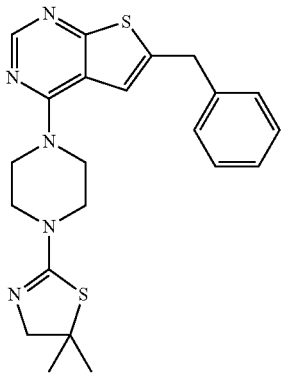 [SMILES: CC1(C)CN=C(N2CCN(c3ncnc4sc(Cc5ccccc5)cc34)CC2)S1] | 4.6 | synthesized |

TABLE 2-continued

Structures and activities for thienopyrimidine class of compounds.

| ID | Structure | IC$_{50}$ (μM) | Vendor cat # |
|---|---|---|---|
| Compound 72 | 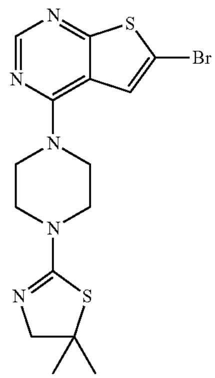 [SMILES: CC1(C)CN=C(N2CCN(c3ncnc4sc(Br)cc34)CC2)S1] | 4.8 | synthesized |
| Compound 73 | 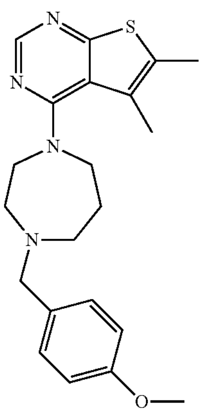 [SMILES: COc1ccc(CN2CCCN(c3ncnc4sc(C)c(C)c34)CC2)cc1] | 20 | Enamine T5902760 |
| Compound 74 | 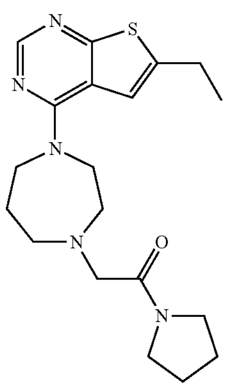 [SMILES: CCc1cc2c(N3CCCN(CC(=O)N4CCCC4)CC3)ncnc2s1] | 7 | Enamine T6210441 |
| Compound 75 | 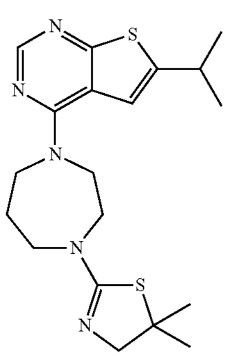 [SMILES: CC(C)c1cc2c(N3CCCN(C4=NCC(C)(C)S4)CC3)ncnc2s1] | 32 | synthesized |

TABLE 2-continued

Structures and activities for thienopyrimidine class of compounds.

| ID | Structure | IC$_{50}$ (μM) | Vendor cat # |
|---|---|---|---|
| Compound 76 | 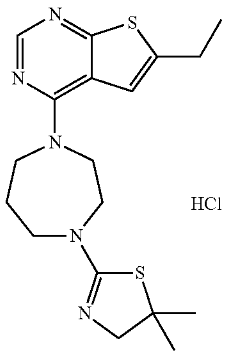 [SMILES: CCc1cc2c(N3CCCN(C4=NCC(C)(C)S4)CC3)ncnc2s1 ; Cl] | 6.3 | synthesized |
| Compound 77 | 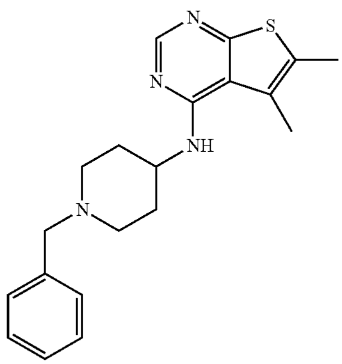 [SMILES: Cc1sc2ncnc(NC3CCN(Cc4ccccc4)CC3)c2c1C] | 8.7 | ChemDiv G786-0963 |
| Compound 78 | 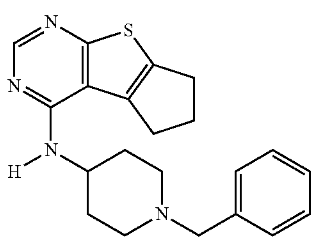 [SMILES: c1ccc(CN2CCC(Nc3ncnc4sc5c(c34)CCC5)CC2)cc1] | 12 | Enamine T0518-1385 |
| Compound 79 | 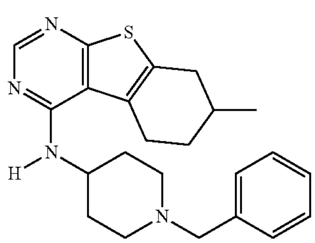 [SMILES: CC1CCc2c(sc3ncnc(NC4CCN(Cc5ccccc5)CC4)c23)C1] | 20 | Enamine T5225244 |
| Compound 80 | 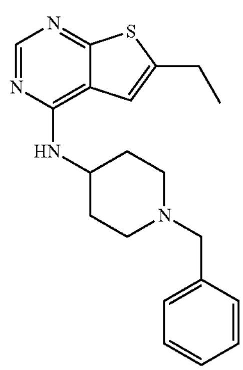 [SMILES: CCc1cc2c(NC3CCN(Cc4ccccc4)CC3)ncnc2s1] | 1.3 | ChemDiv G887-0164 |

TABLE 2-continued

Structures and activities for thienopyrimidine class of compounds.

| ID | Structure | IC$_{50}$ (μM) | Vendor cat # |
|---|---|---|---|
| Compound 81 | 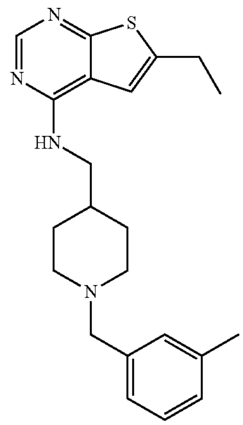 [SMILES: CCc1cc2c(NCC3CCN(Cc4cccc(C)c4)CC3)ncnc2s1] | 40 | ChemDiv G887-0168 |
| Compound 82 | 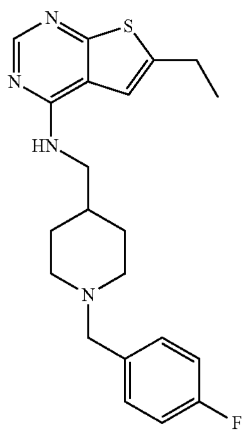 [SMILES: CCc1cc2c(NCC3CCN(Cc4ccc(F)cc4)CC3)ncnc2s1] | 4.4 | ChemDiv G887-0335 |
| Compound 83 | 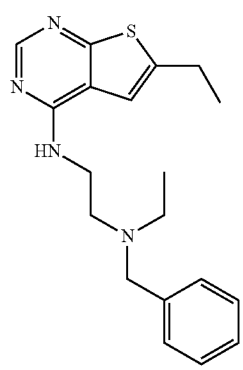 [SMILES: CCc1cc2c(NCCN(CC)Cc3ccccc3)ncnc2s1] | 27 | ChemDiv G887-0354 |

NA—no activity,
NS—no saturation on titration curve.
IC$_{50}$ values < 100 μM are in bold.

Binding of thienopyrimidine compounds to menin measured by NMR. Thienopyrimidine compounds active in inhibiting the MLL binding to menin in FP and HTRF assays were tested in NMR experiments to confirm their direct binding to menin and exclude any promiscuous inhibition (e.g. caused by aggregation, protein unfolding, precipitation, etc.). NMR ligand detecting methods (e.g. STD, competition STD, WaterLOGSY, etc) were used to confirm their binding to menin (SEE FIG. 1A for representative spectra for Compound 1).

Synthesis of thienopyrimidine compounds. Compounds 65-72 were synthesized according to the synthetic Scheme 1. The condensation of aldehyde 1 with ethyl cyanoacetate 2 and elemental sulfur using triethyl amine as a base (Gewald reaction) afforded thiophene 3. Treatments of compound 3 with formamide 4 under heating conditions (120° C.) lead to the formation of thienopyrimidine 5. Chlorination was achieved by refluxing compound 5 in oxalyl chloride to yield compound 6. Nucleophilic substitution of 6 with piperazine 7 provided compound 8, which was then converted to the HCl salt 9.

Scheme 1. Synthetic scheme for thienopyrimidine compounds.

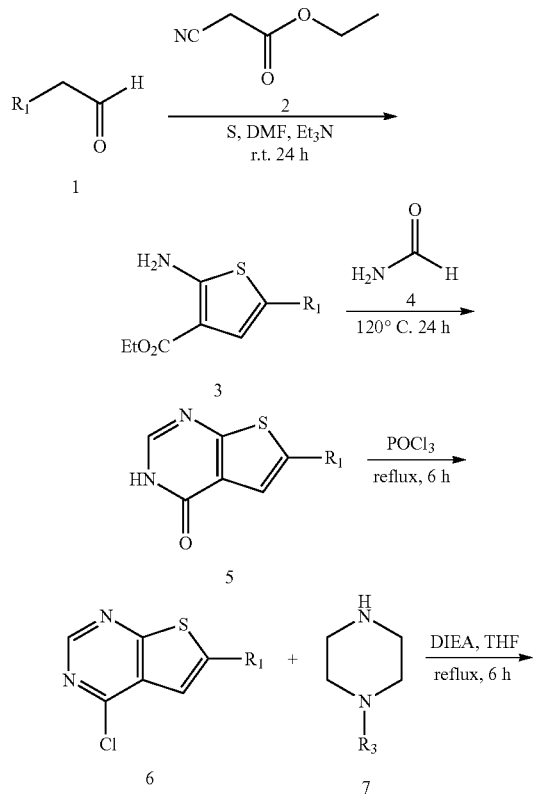

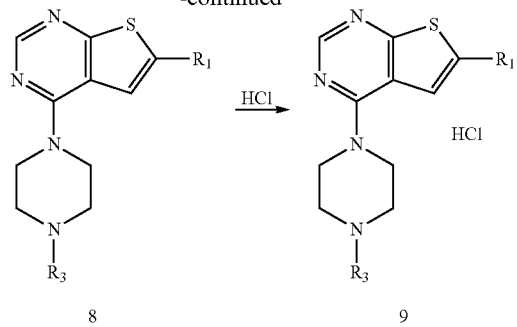

EXAMPLE 3

Elaboration of Benzodiazepine Class of Compounds

Compound 32 has demonstrated the most efficient inhibition from the benzodiazepine class of compounds identified by HTS. Compound 32 was re-tested by FP and HTRF for its inhibition of the menin-MLL interaction, resulting in $IC_{50}$=13 µM (Table 3). Two structurally related compounds identified in primary screening were also re-tested (Compound 33 and Compound 34, Table 3). In addition, compounds from the library with 85% similarity to Compound 32, which were not found as hits in primary screening, were re-tested in dose response curves for their inhibition of the menin-MLL interaction, resulting in as number of active compounds (Table 3). Table 3 lists $IC_{50}$ data for a number of active compounds from the benzodiazepine class. 12 commercially available analogues of Compound 32 were ordered and tested, resulting in one compound with a better $IC_{50}$ (Compound 86, $IC_{50}$=7.4 µM) than the original compound. Active compounds are shown in Table 3.

TABLE 3

Structures and activities for benzodiazepine class of compounds measured by FP and HTRF.

| Compound | Structure | $IC_{50}$ in FP assay with FLSN-MLL (µM) | Vendor/Cat # | $IC_{50}$ in HTRF assay (µM) |
|---|---|---|---|---|
| Compound 32 | 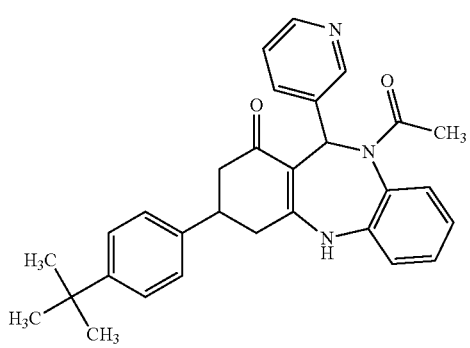 [SMILES: CC(=O)N1c2ccccc2NC2=C(C(=O)CC(c3ccc(C(C)(C)C)cc3)C2)C1c1cccnc1] | 13 | ChemDiv Inc. Cat # 4780-0051 | 7 |

TABLE 3-continued

Structures and activities for benzodiazepine class of compounds measured by FP and HTRF.

| Compound | Structure | IC$_{50}$ in FP assay with FLSN-MLL (μM) | Vendor/Cat # | IC$_{50}$ in HTRF assay (μM) |
|---|---|---|---|---|
| Compound 33 | 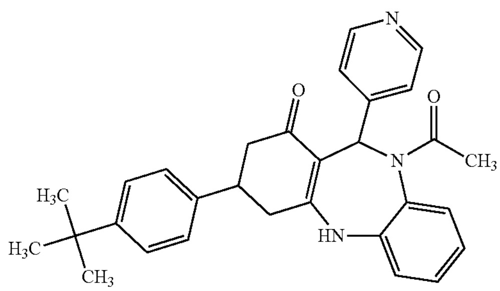 [SMILES: CC(=O)N1c2ccccc2NC2=C(C(=O)CC(c3ccc(C(C)(C)C)cc3)C2)C1c1ccncc1] | 29 | ChemDiv Inc. Cat # 5742-0717 | 28 |
| Compound 34 | 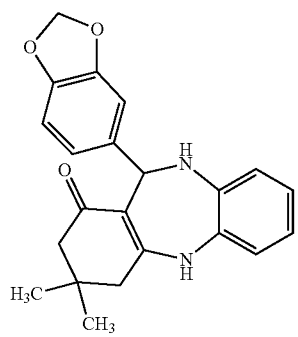 [SMILES: CC1(C)CC(=O)C2=C(C1)Nc1ccccc1NC2c1ccc2c(c1)OCO2] | 12 | ChemDiv Inc. Cat # 3393-0109 | ND |
| Compound 35 | 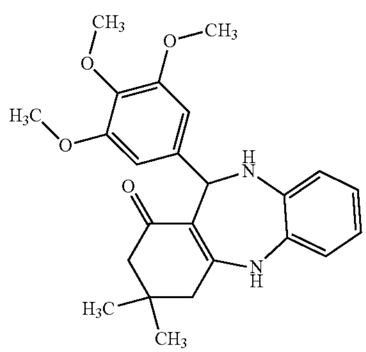 [SMILES: COc1cc(C2Nc3ccccc3NC3=C2C(=O)CC(C)(C)C3)cc(OC)c1OC] | 35 | ChemDiv Inc. Cat # 3393-0126 | ND |
| Compound 36 | 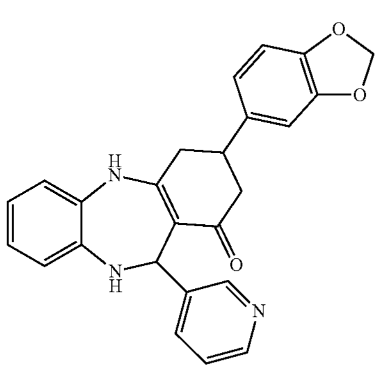 [SMILES: O=C1CC(c2ccc3c(c2)OCO3)CC2=C1C(c1cccnc1)Nc1ccccc1N2] | 63 | ChemDiv Inc. Cat # 3170-5216 | ND |

TABLE 3-continued

Structures and activities for benzodiazepine class of compounds measured by FP and HTRF.

| Compound | Structure | IC$_{50}$ in FP assay with FLSN-MLL (μM) | Vendor/Cat # | IC$_{50}$ in HTRF assay (μM) |
|---|---|---|---|---|
| Compound 37 | 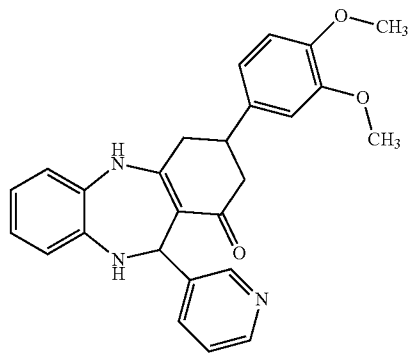 [SMILES: COc1ccc(C2CC(=O)C3=C(C2)Nc2ccccc2NC3c2cccnc2)cc1OC] | 100 | ChemDiv Inc. Cat # 3404-5359 | ND |
| Compound 38 | 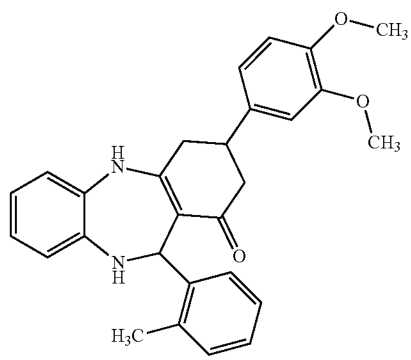 [SMILES: COc1ccc(C2CC(=O)C3=C(C2)Nc2ccccc2NC3c2ccccc2C)cc1OC] | 115 | ChemBridge Cat # 6369841 | ND |
| Compound 39 | 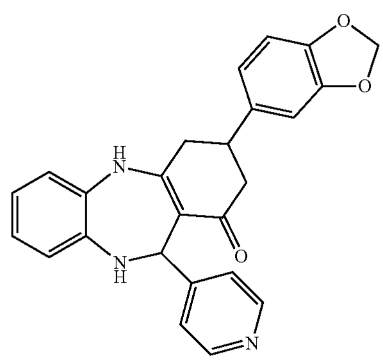 [SMILES: O=C1CC(c2ccc3c(c2)OCO3)CC2=C1C(c1ccncc1)Nc1ccccc1N2] | 230 | ChemDiv Inc. Cat # 3170-5232 | ND |
| Compound 40 | 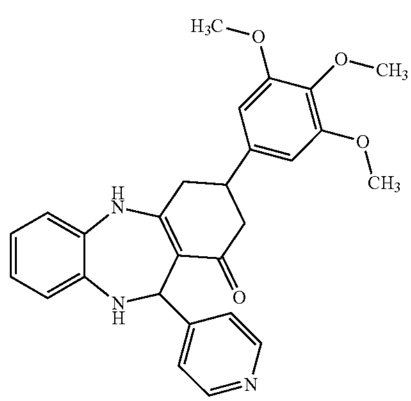 [SMILES: COc1cc(C2CC(=O)C3=C(C2)Nc2ccccc2NC3c2ccncc2)cc(OC)c1OC] | NA | ChemDiv Inc. Cat # 5531-8211 | ND |

TABLE 3-continued

Structures and activities for benzodiazepine class of compounds measured by FP and HTRF.

| Compound | Structure | IC$_{50}$ in FP assay with FLSN-MLL (μM) | Vendor/Cat # | IC$_{50}$ in HTRF assay (μM) |
|---|---|---|---|---|
| Compound 41 | 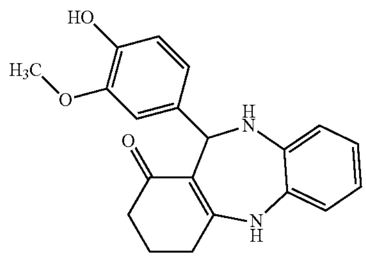 [SMILES: COc1cc(C2Nc3ccccc3NC3=C2C(=O)CCC3)ccc1O] | NA | ChemDiv Inc. Cat # 3770-0060 | ND |
| Compound 84 | 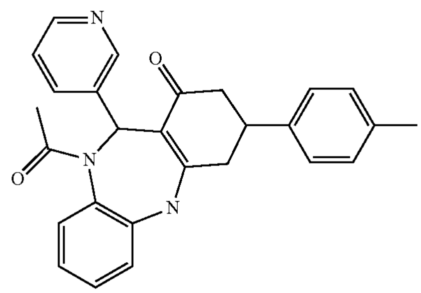 [SMILES: CC(=O)N1c2ccccc2NC2=C(C(=O)CC(c3ccc(C)cc3)C2)C1c1cccnc1] | 100 | Interbioscreen STOCK2S-89112 | ND |
| Compound 85 | 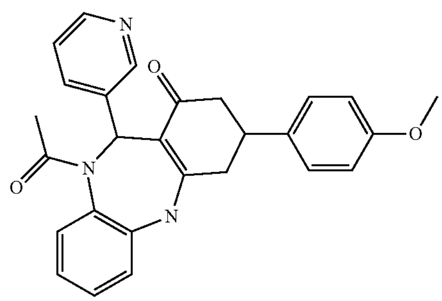 [SMILES: COc1ccc(C2CC(=O)C3=C(C2)Nc2ccccc2N(C(C)=O)C3c2cccnc2)cc1] | 72 | ChemBridge 8879201 | ND |
| Compound 86 | 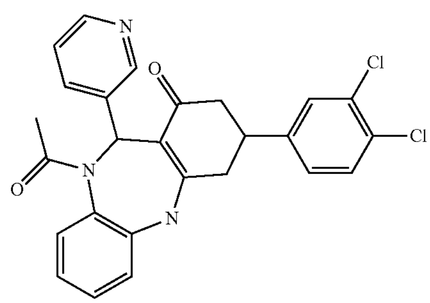 [SMILES: CC(=O)N1c2ccccc2NC2=C(C(=O)CC(c3ccc(Cl)c(Cl)c3)C2)C1c1cccnc1] | 7.4 | ChemBridge 8879215 | ND |

NA—no activity,
ND—not determined,
IC$_{50}$ values < 100 μM are in bold.

Binding of benzodiazepine compounds to menin measured by NMR. Benzodiazepine compounds active in inhibiting the MLL binding to menin in FP and HTRF assays were tested in NMR experiments to confirm their direct binding to menin and exclude any promiscuous inhibition (e.g. caused by aggregation, protein unfolding, precipitation, other non-specific effects, etc.). The NMR ligand detecting methods (e.g. STD, competition STD, WaterLOGSY, etc.) were used to confirm their binding to menin (SEE FIG. 1B for representative spectra for Compound 33).

EXAMPLE 4

In Vivo Compound Testing

Figure 2:
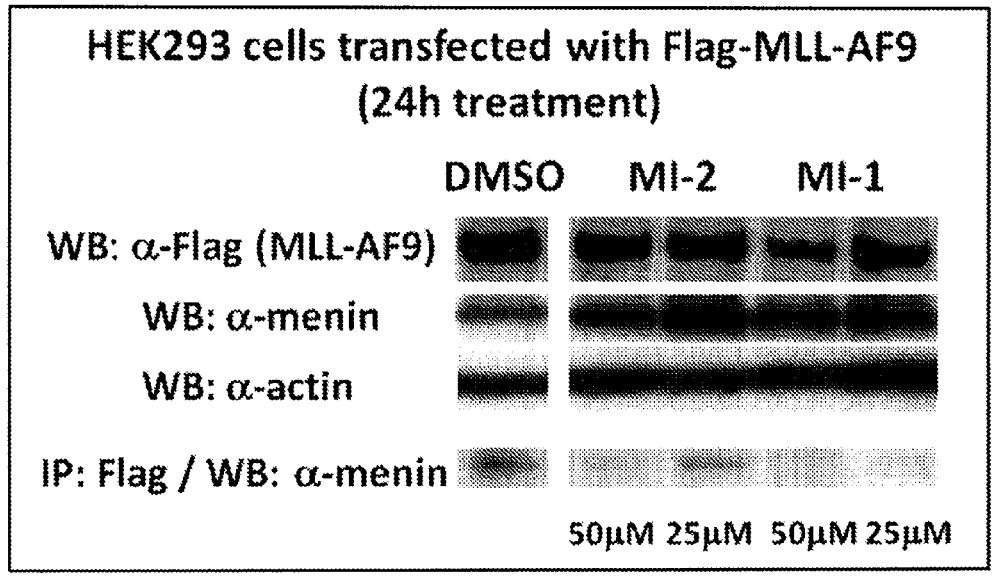
FIG. 2. A. Co-Immunoprecipitation experiments in HEK293 cells transfected with Flag-MLL-AF9 treated with thienopyrimidine compound (MI-1=Compound 64) and benzodiazepine compound (MI-2=Compound 33) after 24 h incubation with each compound. B. Co-Immunoprecipitation experiments in HEK293 cells transfected with Flag-MLL-AF9 and treated with the most potent thienopyrimidine compounds: RJS-4-020=Compound 67, and AS-1-19=Compound 70 after 6h incubation with each compound.
Figure 2:
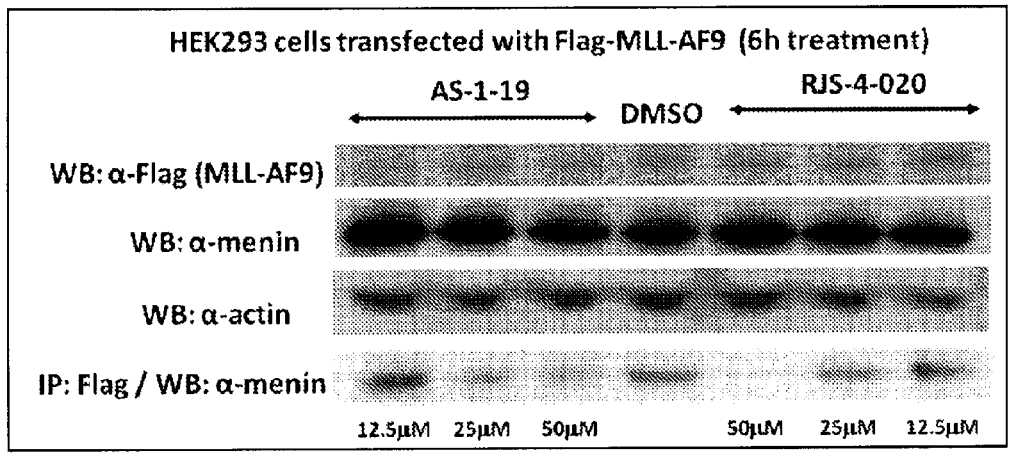

Inhibition of the menin-MLL interaction in human cells. Thienopyrimidine (Compound 64 labeled as MI-1, Compound 67 labeled as RJS-4-020, Compound 70 labeled as AS-1-19) and benzodiazepiene (Compound 32 labeled as MI-2 or CCG-21196) compounds were tested for their inhibition of the menin-MLL interaction in HEK293 cells transfected with Flag-MLL-AF9 by applying the co-Immunoprecipitation experiments (SEE FIG. 2). Both classes of compounds can effectively inhibit this interaction in human cells at 50 µM and 25 µM compound concentration as compared to the DMSO control, demonstrating their potential as drug candidates for further development.

Figure 3:
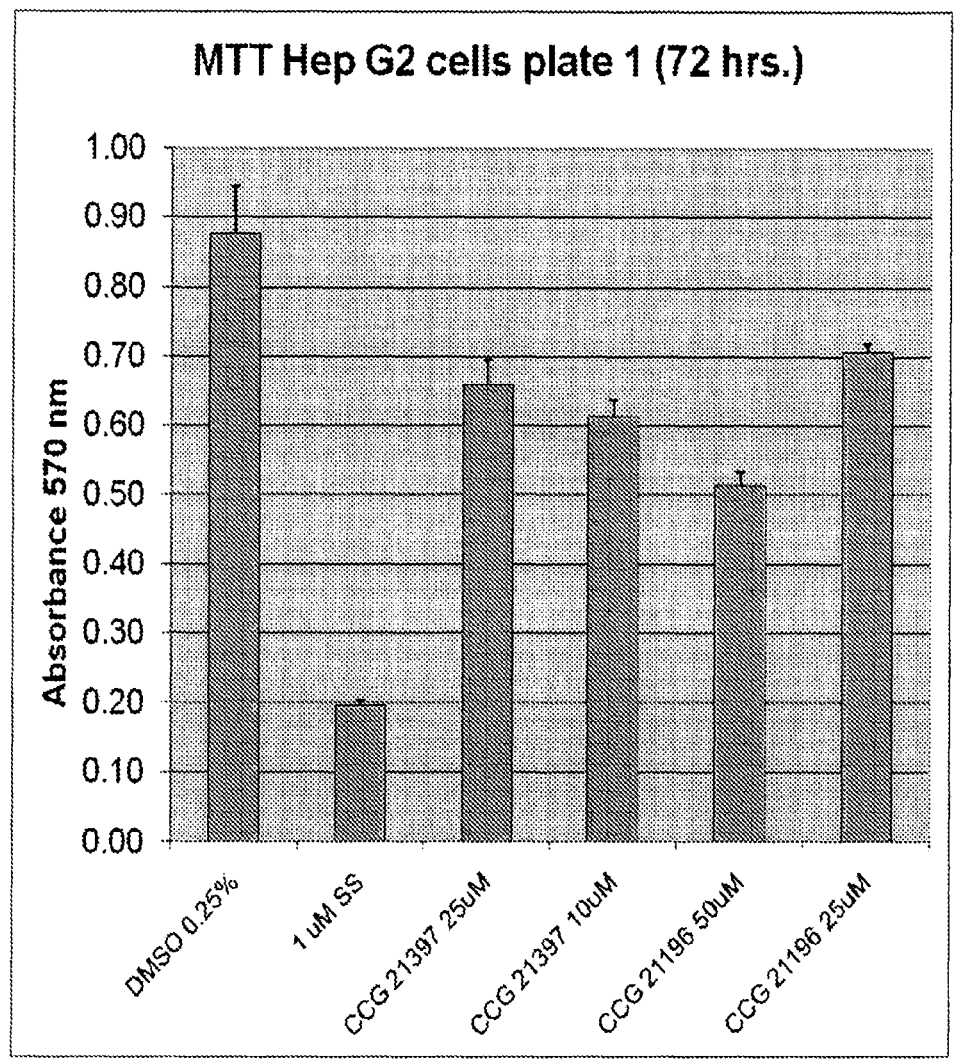
FIG. 3. MTT viability assay of benzodiazepine (CCG-21196=Compound 33) and thienopyrimidine (CCG-21397=Compound 1 and CCG-21397-25=Compound 4) compounds in human liver (HepG2) and kidney (HK-2) cell lines showing no substantial signs of toxicity for these compounds.
Figure 3:
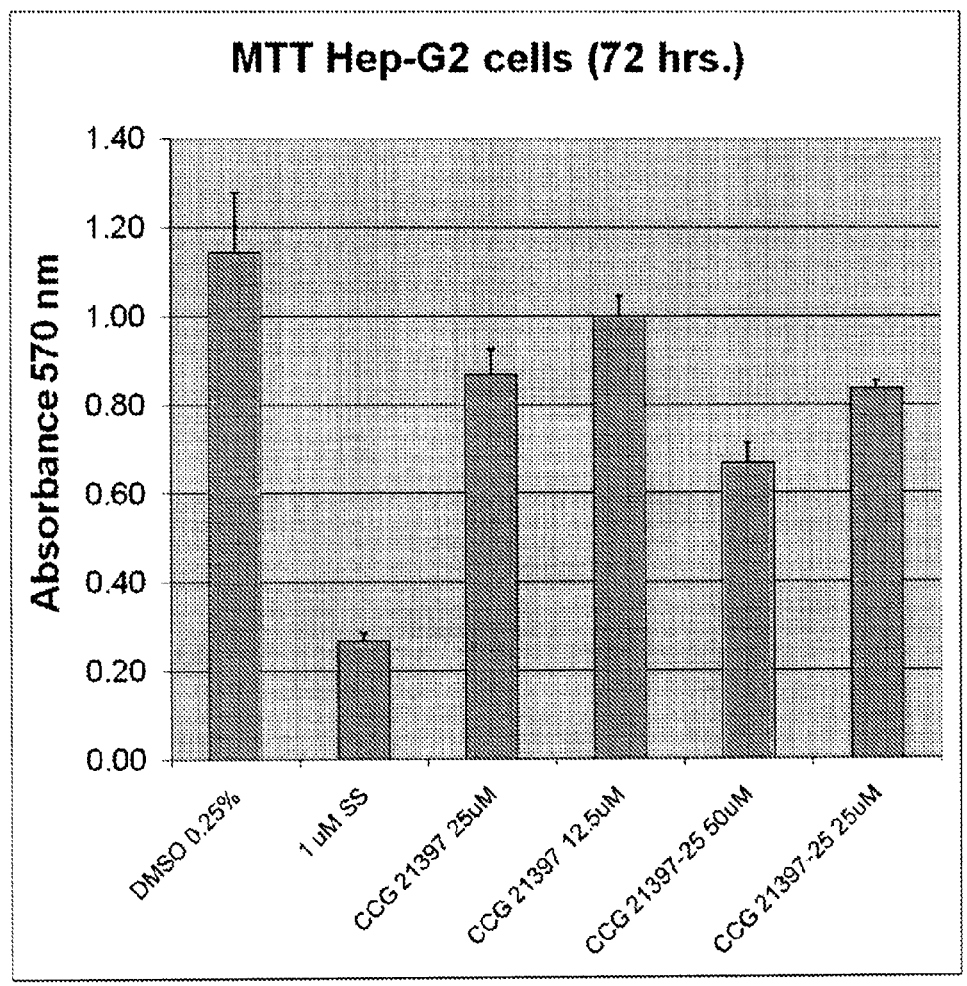
Figure 3:
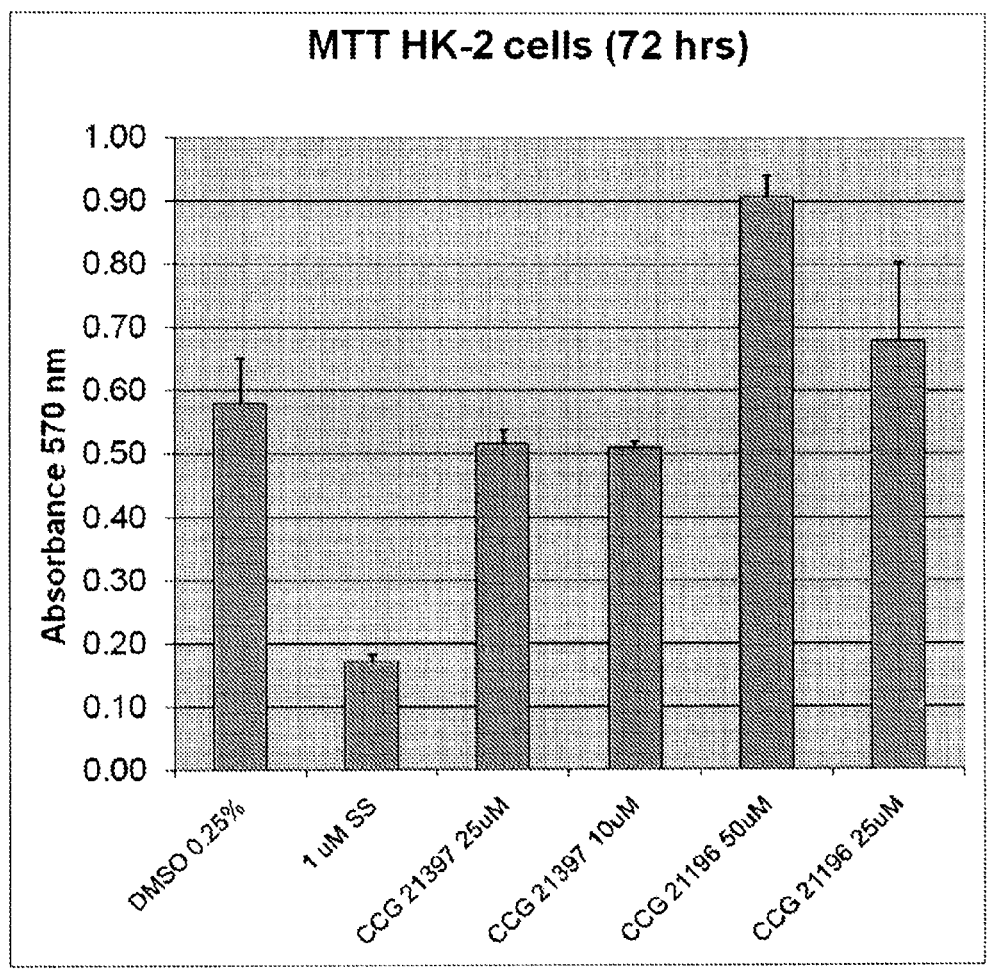

Effects of thienopyrimidine and benzodiazepine compounds in kidney and liver cell lines. The effectiveness of compounds from thienopyrimidine and benzodiazepine classes were tested in human cell lines. Effects on cell growth were assayed using the MTT viability assay (Mosmann. Immunol Methods., 1983; 65(1-2):55-63, herein incorporated by reference in its entirety). The viability assay (MIT) with Hep-G2 (liver) and HK-2 (kidney) cell lines resulted in no signs of substantial toxicity for both classes of compounds (SEE FIG. 3. Compound 1 labeled as CCG_21397, Compounds 4 labeled as CCG_21397_25, Compound 32 labeled as CCG 21196).

Figure 4:
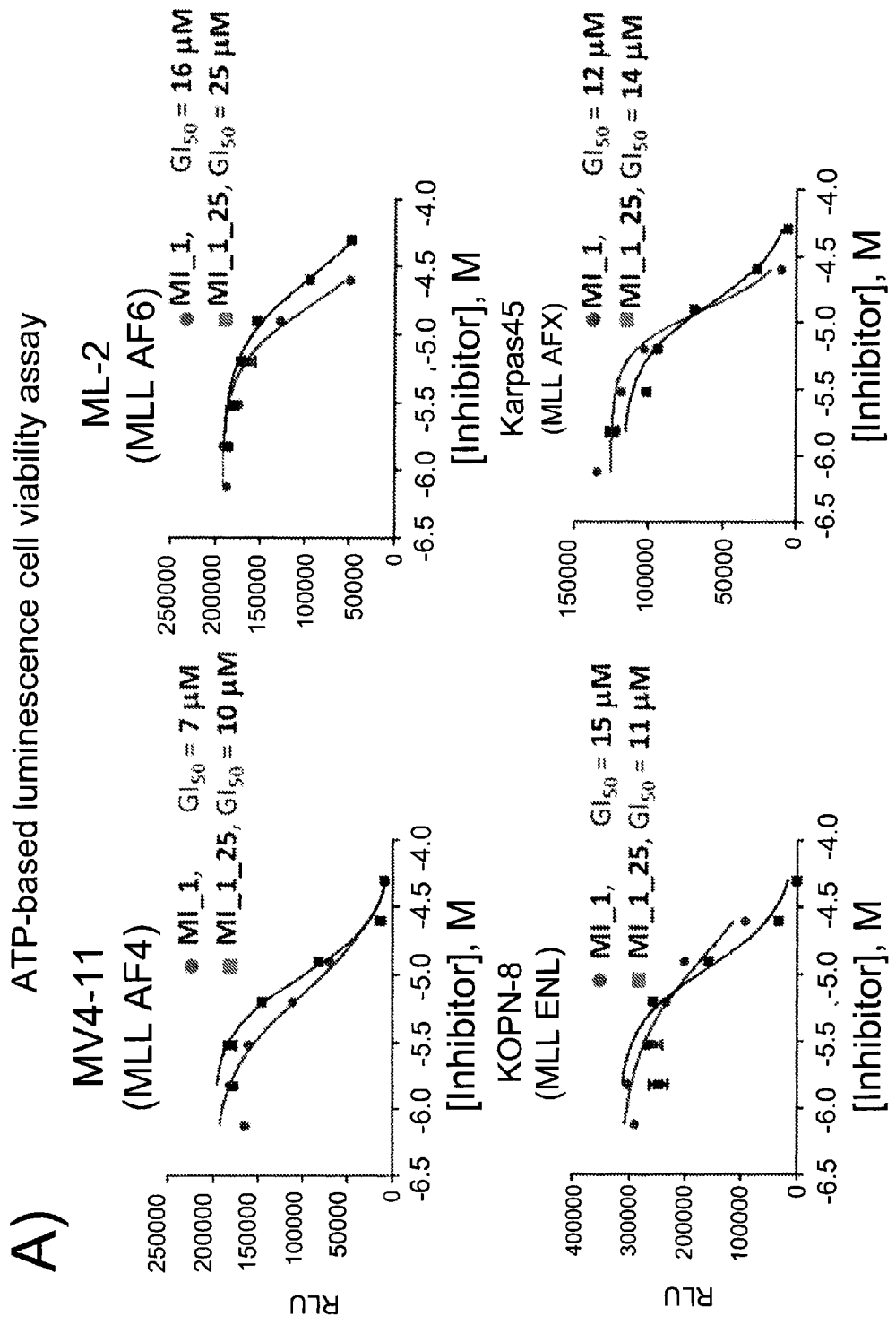
FIG. 4. A. ATP-based luminescence cell viability assay in human leukemia cell lines with different MLL translocations (MV4; 11-MLL-AF4; ML-2-MLL-AF6; KONP8-MLL-ENL; Karpas45-MLL-AFX) treated with thienopyrimidine compounds (MI-1=Compound 64 and MI-1-25=Compound 4) demonstrating substantial growth inhibition of MLL leukemia cells. B. MTT viability assay for the most potent thienopyrimidine compound (AS-1-19=Compound 70) in human leukemia cell lines with MLL translocations (MV4; 11 harboring MLL-AF4 fusion and MonoMac6 harboring MLL-AF9 fusion protein).
Figure 4:
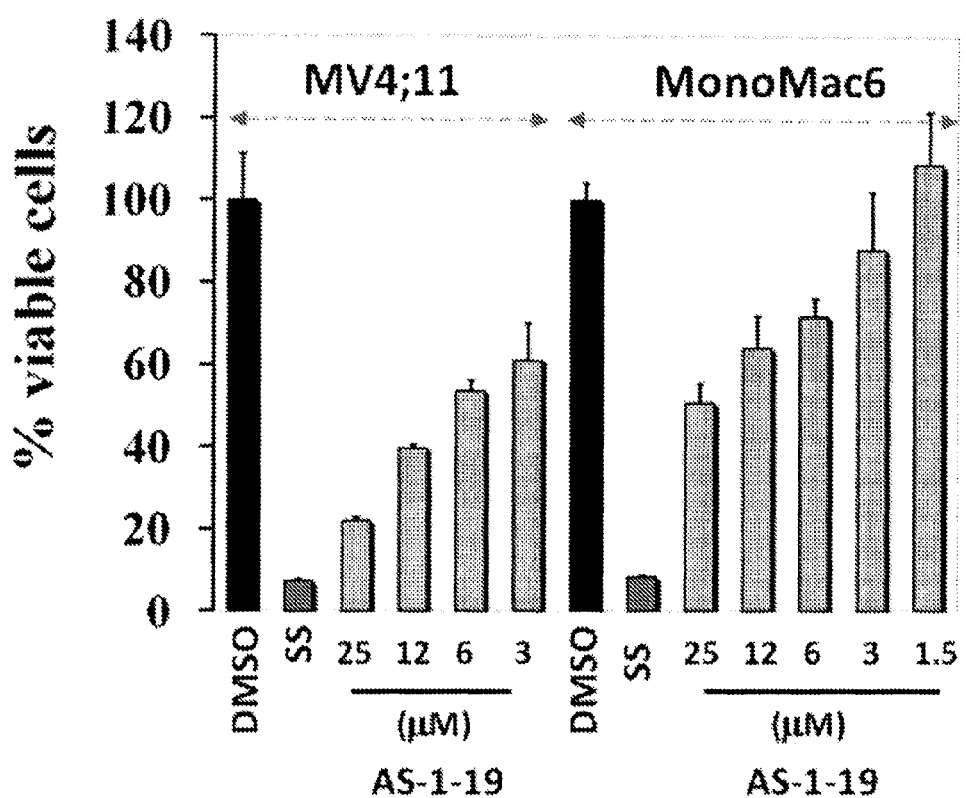

Effects of thienopyrimidine and benzodiazepine compounds on growth inhibition of human leukemia cell lines with MLL translocations. Viability assay in human leukemia cell lines was performed with representative compounds from thienopyrimidine and benzodiazepine classes. Several cell lines, including the MV4; 11, ML-2, KOPN-8, Karpas 45, MonoMac6 cell lines harboring different MLL translocation, were tested to evaluate compound effectiveness in inhibiting the growth of human leukemia cell lines. Very effective growth inhibition of human leukemia cell lines was observed for thienopyrimidine class of compounds:—Compound 64 (labeled as CCG_21397 or MI-1), Compound 4 (labeled as CCG_21397_25 or MI-1-25) (SEE FIG. 4A), with the $GI_{50}$ values at low micromolar range: 7-25 µM, and for Compound 70 (labeled as AS-1-19) (SEE FIG. 4B), which is the most potent compound out of thienopyrimidine class in in vitro FP experiment (Tables 1 and 2).

Figure 5:
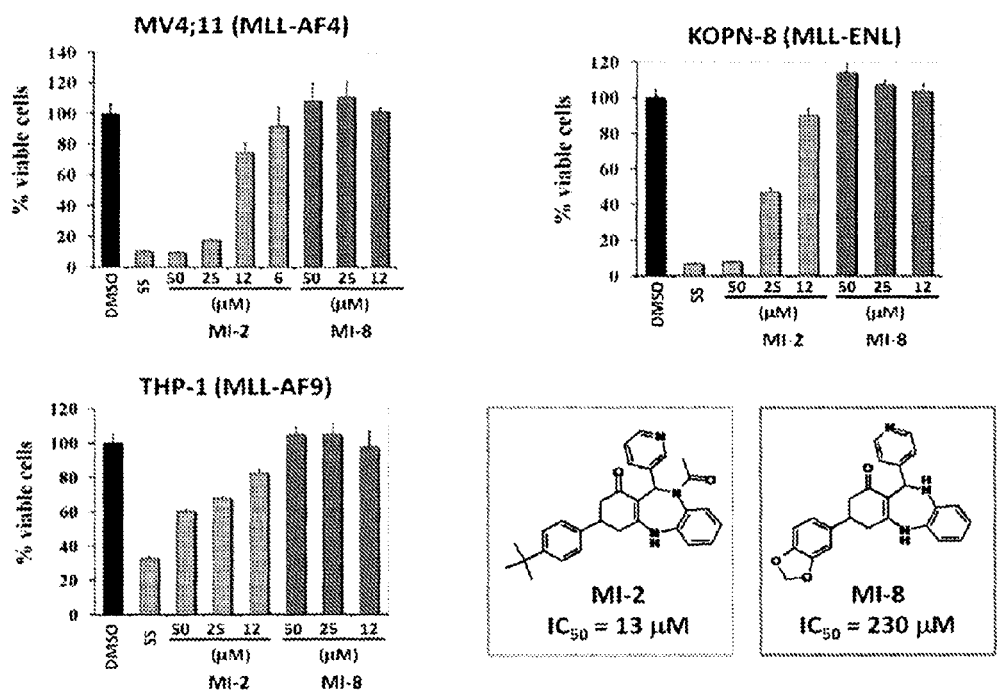
FIG. 5. A. MTT cell viability assay in human leukemia cell lines with different MLL translocations (MV4; 11-MLL-AF4; KONP8-MLL-ENL; THP-1-MLL-AF9) treated with benzodiazepine compounds (MI-2=Compound 32 and MI-8=Compound 39) demonstrating substantial growth inhibition of MLL leukemia cells by Compound 32 and no effect for Compound 39. These results correlate very well with the in vitro $IC_{50}$ values for these compounds. B. MTT viability assay for the most potent benzodiazepine compound (MI-2-12=Compound 86) in human leukemia cell lines with MLL translocations (MV4; 11 harboring MLL-AF4 fusion and MonoMac6 harboring MLL-AF9 fusion protein).
Figure 5:
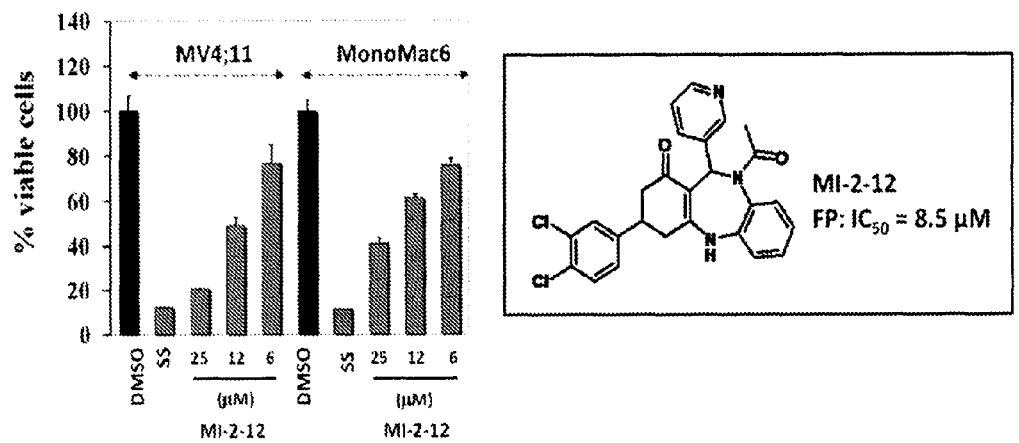

Benzodiazepine compounds, including Compound 32 (labeled as CCG_21196 or MI-2), and Compound 86 (labeled as MI-2-12) also strongly inhibited growth of the MLL leukemia cells (SEE FIG. 5). In contrast, Compound 39 (labeled as MI-8), which was used as a negative control, showed no growth inhibition of the MLL leukemia cells, which correlates very well with the in vitro $IC_{50}$ value for this compound.

Figure 6:
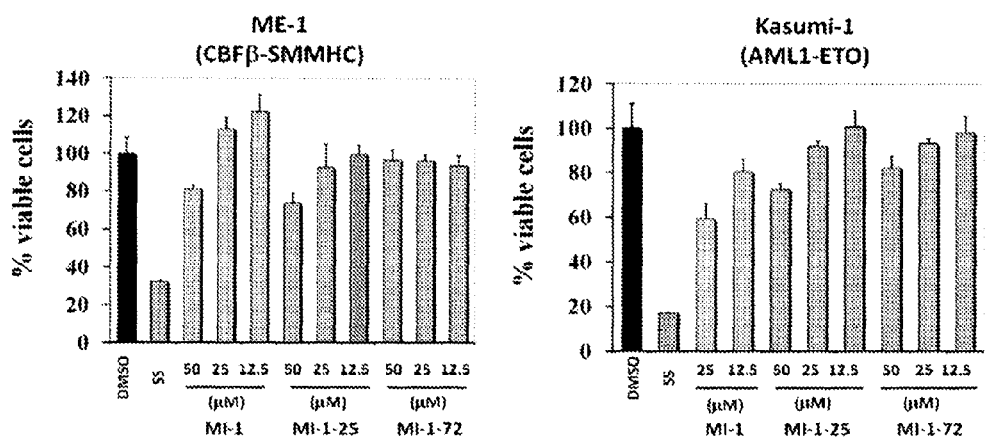
FIG. 6. A. MIT cell viability assay with thienopyrimidine compounds (Compound 64=MI-1, Compound 4=MI-1-25 and Compound 63=MI-1-72) in non-MLL leukemia cell lines (Kasumi-1 harboring AML1-ETO and ME-1 harboring CBFβ-SMMHC fusion proteins). No or very limited effect is observed, confirming selectivity of these compounds to MLL-leukemia cell lines. B. MTT cell viability assay with the most potent thienopyrimidine compound (Compound 70=AS-1-19) in non-MLL leukemia cell lines (Kasumi-1 harboring AML1-ETO and ME-1 harboring CBFβ-SMMHC fusion proteins) showing no effect on the cell growth, demonstrating selectivity of this compound to the MLL-leukemia cells. C. MIT cell viability assay with the most potent benzodiazepine compound (Compounds 86=MI-2-12) in non-MLL leukemia cell lines (Kasumi-1 and ME-1) showing no or very limited effect on cell growth.
Figure 6:
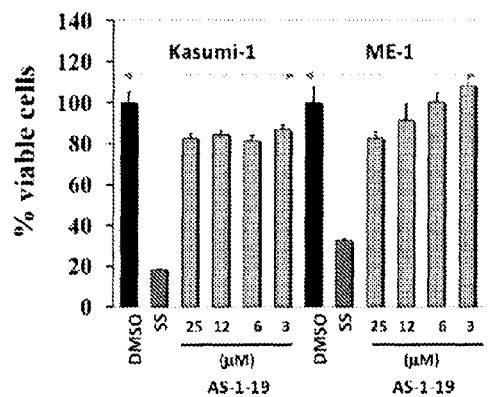
Figure 6:
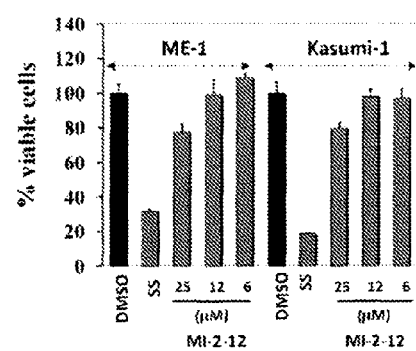

Specificity of thienopyrimidine and benzodiazepine compounds to MLL leukemia cells. Thienopyrimidine and benzodiazepiene compounds were tested in MTT viability assay to assess their effect on the growth of other leukemia cell lines without MLL translocations. Limited or no effect were observed for both classes of compounds (SEE FIG. 6), demonstrating their selectivity for inhibiting the growth of MLL fusion cell lines.

Figure 7:
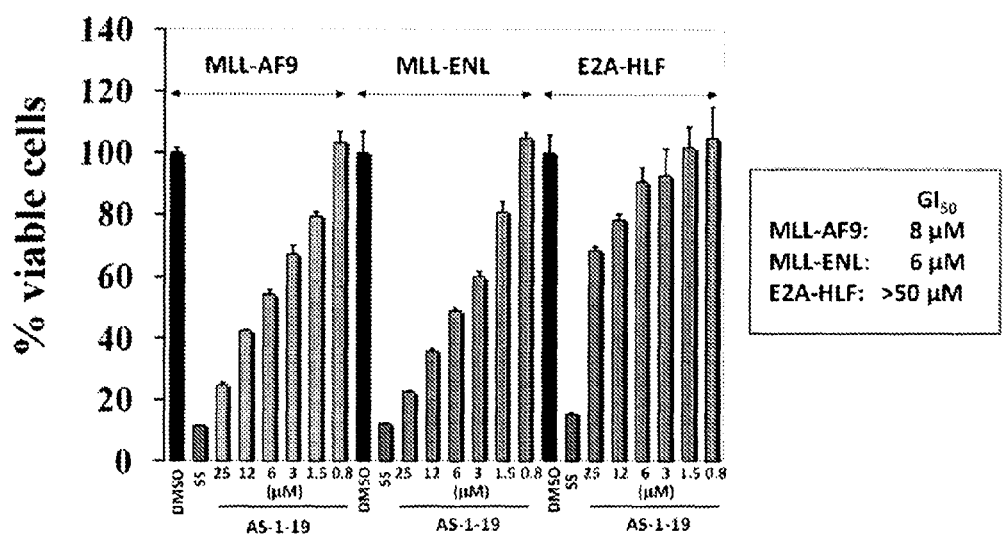
FIG. 7. MTT viability assay with thienopyrimidine compound (Compound 70=AS-1-19) in mouse bone marrow transduced with MLL-AF9, MLL-ENL and E2A-HLF (pro-B cell leukemia used as a negative control), demonstrating selectivity in inhibiting the growth of MLL fusion transduced mouse bone marrow.

Effects of thienopyrimidine compounds on mouse bone marrow transduced with MLL-AF9 and MLL-ENL. Thienopyrimidine compound (Compound 70 is AS-1-19) exhibits substantial inhibition of cell growth in mouse bone marrow transduced with MLL-AF9 and MLL-ENL fusion protein as measured by MTT cell viability assay (SEE FIG. 7). In contrast, no significant inhibition of cell growth was observed on mouse bone marrow transduced with E2A-HLF (pro-B-cell leukemia) was observed for this compound. This demonstrates again that thienopyrimidine compounds specifically inhibit growth of cells with MLL translocation.

Figure 8:
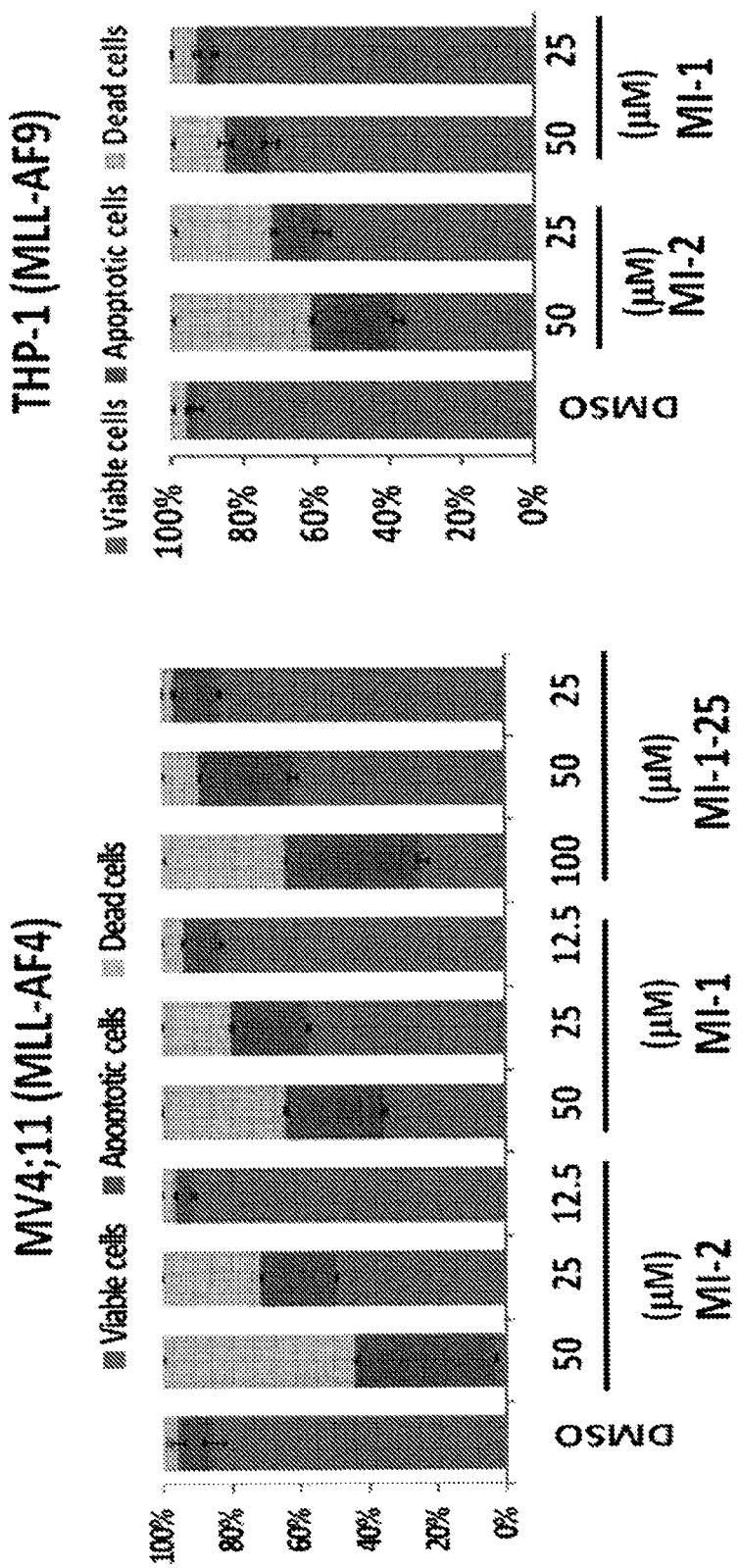
FIG. 8. Annexin V/PI flow cytometry experiments with thienopyrimidine compounds (Compound 64=MI-1, Compound 4=MI-1-25) and benzodiazepine compound (Compound 32=MI-2) in MLL fusion leukemia cell lines (MV4; 11 with MLL-AF4 and THP-1 with MLL-AF9). All compounds induce substantial apoptosis and cell death at 25 μM and 50 μM concentrations.

Thienopyrimidine and benzodiazepine compounds induce apoptosis in MLL leukemia cells. Compounds from both classes were assessed for their ability to induce apoptosis in MLL leukemia cell lines (MV4; 11 and THP-1) using the Annexin V/PI staining flow cytometry experiments (SEE FIG. 8). Both classes of compounds can effectively induce apoptosis and cell death in MLL fusion cells lines at low micromolar concentration (25-50 µM). This effect is more pronounced in MLL-AF4 cells (>20% of apoptotic cells at 25 µM of Compound 64 labeled as MI-1 and Compound 32 labeled as MI-2 and more than 20% of dead cells in the same experimental conditions). In THP-1 MLL leukemia cells, more pronounced effect was observed for benzodiazepine class of compounds: treatment with Compound 32 (labeled as MI-2) resulted in about 20% apoptotic cells and >40% of dead cells at 50 µM compound concentration. Thienopyrimidine Compound 64 (labeled as MI-1) resulted in a less pronounced effect, but apoptosis and cell death were induced as compared to DMSO control (SEE FIG. 8).

Figure 9:
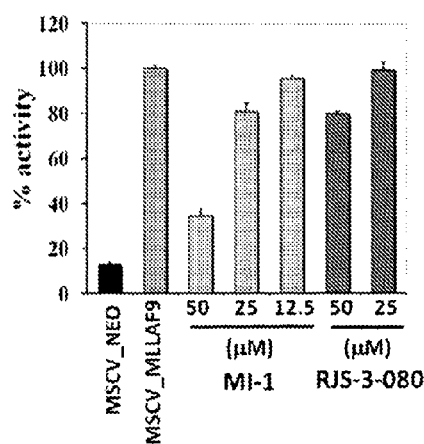
FIG. 9. Luciferase reporter assay performed in HEK293 cells transfected with MLL-AF9 showing the effect of compounds on transactivation of Hoxa9 promoter: A) Inhibition of transactivation of Hoxa9 promoter by thienopyrimidine compound (MI-1=Compound 64, RJS-3-080 was used as a negative control); B) Effect for benzodiazepine compounds (MI-2=Compound 32 showing dose dependent inhibition, MI-8=Compound 39 was used as a negative control).
Figure 9:
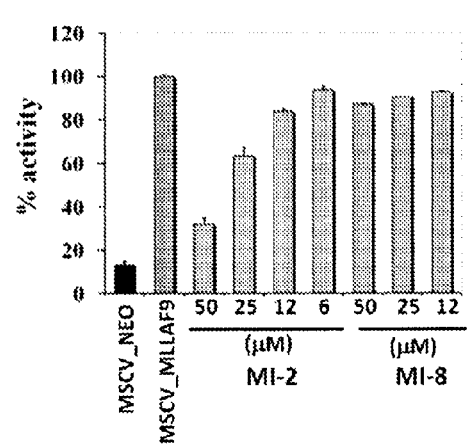
Figure 10:
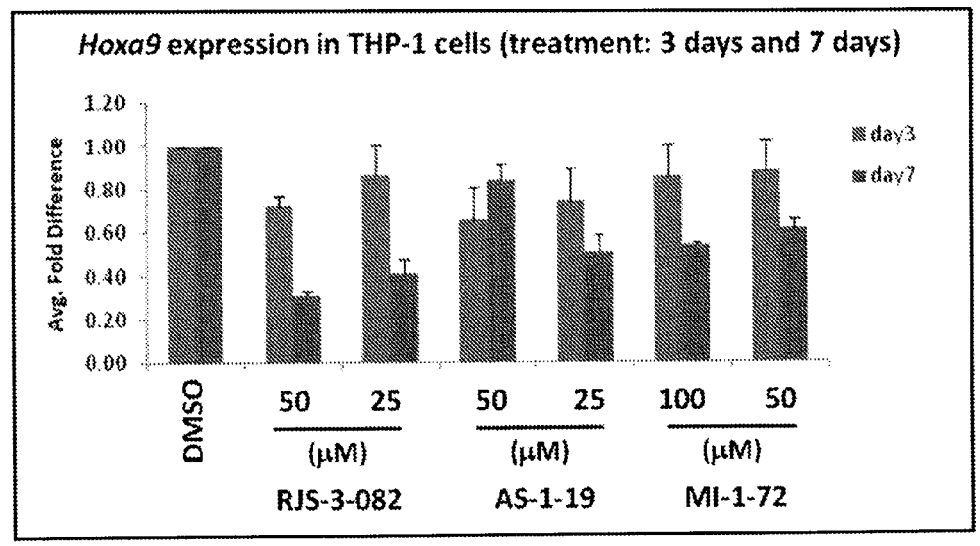
FIG. 10. Effect of compounds on expression level of MLL downstream targets: Hoxa9 and Meis1 in THP-1 leukemia cells as measured by qRT-PCR experiments: A) Downregulation of Compound 70, MI-1-72=Compound 63); B) Downregulation of Hoxa9 and Meis1 expression by benzodiazepine compound (MI-2-12=Compound 86).
Figure 10:
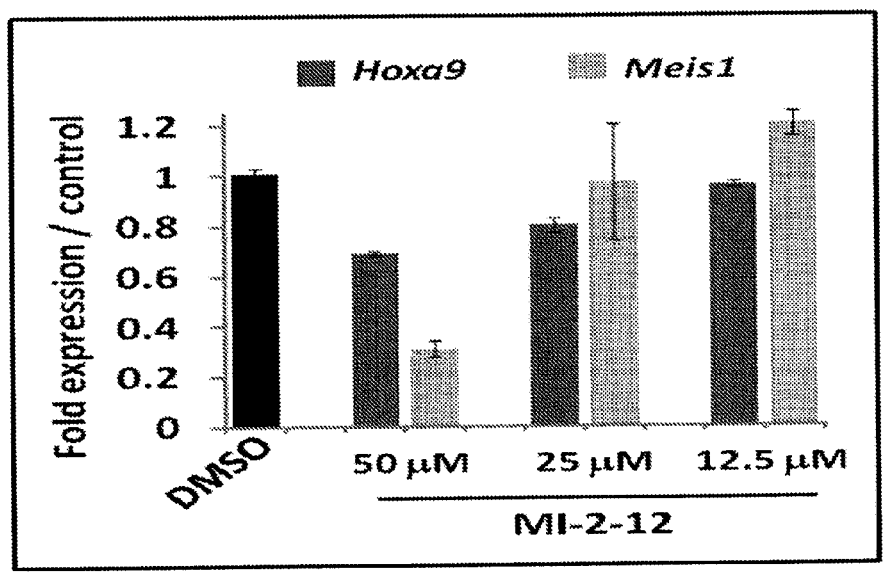

Effect of thienopyrimidine and benzodiazepine compounds on MLL fusion downstream targets Hoxa9 and Meis1. The effect of both classes of compounds on expression of MLL fusion downstream targets was assessed in the luciferase reporter assay (SEE FIG. 9) and by RT-PCR (SEE FIG. 10). Both classes of compounds (Compound 64 labeled as MI-1 and Compound 32 labeled as MI-2) can effectively inhibit the transactivation of the Hoxa9 promoter in the luciferase reporter assay in HEK293 cell transfected with MLL-AF9. No effect was observed for the negative control compounds: (RJS-3-080 and Compound 39 labeled as MI-8), which correlates well with the in vitro $IC_{50}$ values. Furthermore, the downregulation of Hoxa9 expression was also observed in the RT-PCR experiments performed in THP-1 cells for both classes of compounds (SEE FIG. 10), with a more pronounced effect after 7 days of incubation time with compounds. These compounds also decreased the expression level of Meis1, which is another downstream target of MLL (SEE FIG. 10b).

Figure 11:
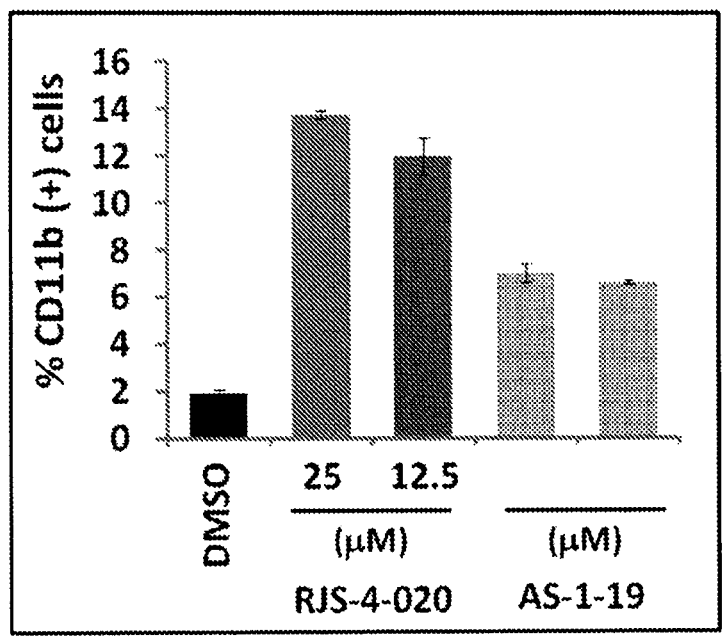
FIG. 11. Differentiation of THP-1 leukemia cells measured by the expression level of CD11b using flow cytometry: A) Effect for thienopyrimidine compounds (RJS-4-020=Compound 67, AS-1-19=Compound 70); B) Benzodiazepine compound (MI-2=Compound 32).
Figure 11:
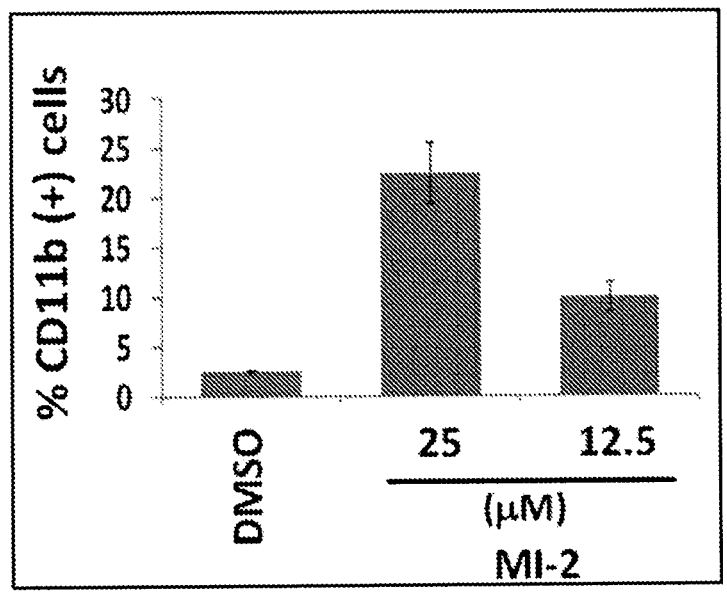

Thienopyrimidine and benzodiazepine compounds induce differentiation of the MLL leukemia cells. Treatment of THP-1 leukemia cells with thienopyrimidine (Compound 67 labeled as RJS-4-020 and Compound 70 labeled as AS-1-19) and benzodiazepine (Compound 32 labeled as MI-2) results in increased expression of CD11b on the cell surface (SEE FIG. 11), indicative of differentiation of these cells in response to compound treatment.

EXAMPLE 5

Additional Compounds

Experiments were conducted to screen a subset of the Maybridge fragment library (MFL) (500 compounds with diverse molecular scaffolds, drug-like properties and molecular weight below 300 Da) using the FP assay. The MFL was screened for the competitive displacement of the fluorescein-labeled MLL peptide from menin using FP.

Figure 12:
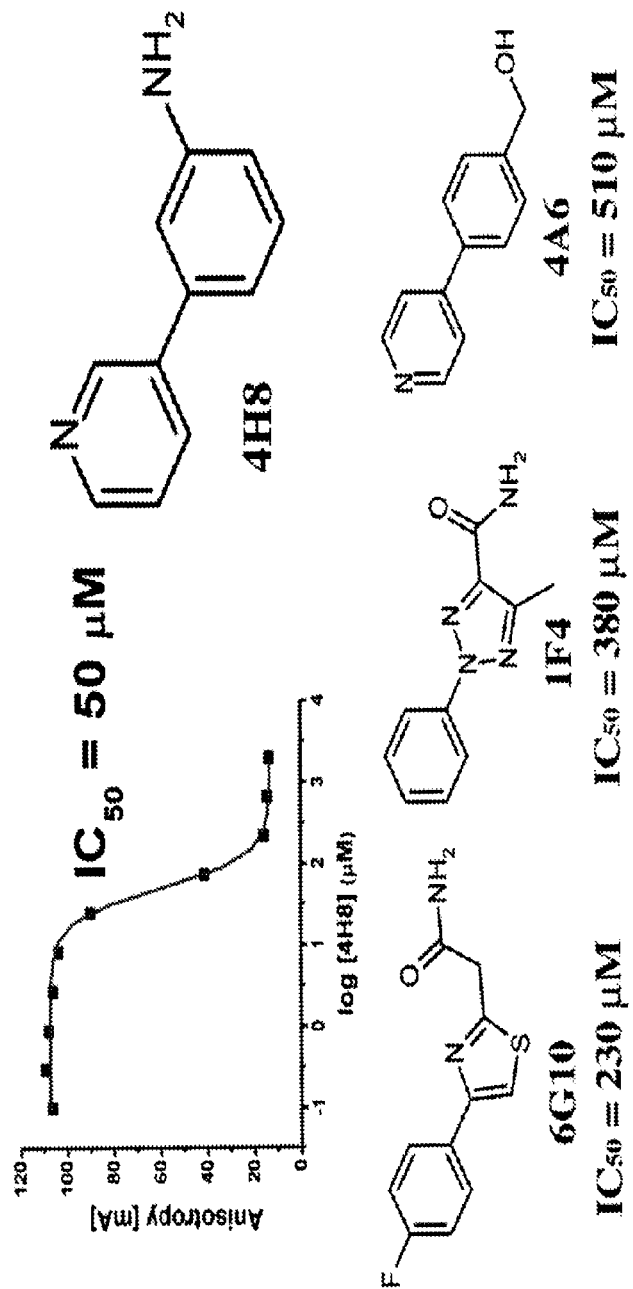
FIG. 12. Determination of $IC_{50}$ by NMR spectroscopy.

The screening of the MFL resulted in 20 compounds showing >25% inhibition of the MLL peptide binding to menin at 500 µM concentration, which were subsequently tested in a dose dependent manner to determine the $IC_{50}$ values. Compounds which interfered with the assay (precipitation, intrinsic fluorescence) were considered as false positives and excluded from further analysis. Finally, 11 compounds were obtained with diverse molecular scaffolds which inhibited the menin-MLL interaction with the $IC_{50}$ values below 2 mM. Binding to menin was confirmed for 4 compounds (Compounds 42 (4H8), 43 (6G 10), 44 (1F4), and 45 (4A6) by applying NMR spectroscopy with the most potent compound, Compound 42 ($IC_{50}$=50 µM) (FIG. 12).

Compound 43 analogues have been evaluated to improve their potency in inhibiting the menin-MLL interaction. 15 compounds were tested, with the most active (6G10_3) being about 4 fold more potent than the original hit (Table 4).

TABLE 4

Structures and activities of hits from MFL and 6G10 analogues measured by FP and HTRF.

| Compound | Structure | $IC_{50}$ in FP assay with FLSN-MLL (µM) | Vendor/ Cat # | $IC_{50}$ in HTRF assay (µM) |
|---|---|---|---|---|
| 1F4 Compound 44 | 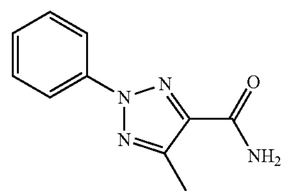 | 380 | Maybridge BTB 03582 | |
| 4H8 Compound 42 | 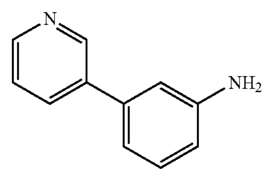 [SMILES: Nc1cccc(-c2cccnc2)c1] | 50 | Maybridge CC39814 | |
| 4A6 Compound 45 | 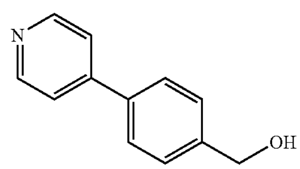 [SMILES: OCc1ccc(-c2ccncc2)cc1] | 510 | Maybridge CC35409 | |
| 6G10 Compound 43 | 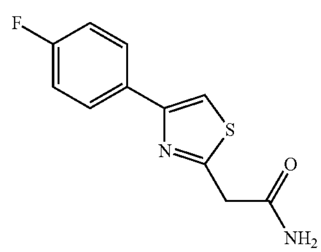 [SMILES: NC(=O)Cc1nc(-c2ccc(F)cc2)cs1] | 230 | ChemBridge Corporation 6956708 | 200 |
| 6G10_1 Compound 46 | 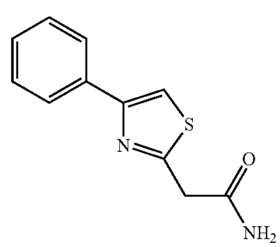 [SMILES: NC(=O)Cc1nc(-c2ccccc2)cs1] | 2000 | Maybridge SB02074 | ND |
| 6G10_3 Compound 47 | 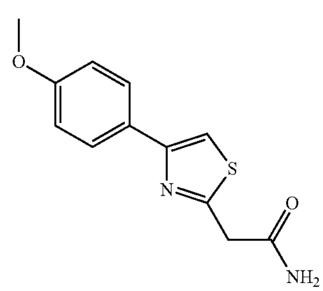 [SMILES: COc1ccc(-c2csc(CC(N)=O)n2)cc1] | 67 | Enamine T5648583 | 33 |

TABLE 4-continued

Structures and activities of hits from MFL and 6G10 analogues measured by FP and HTRF.

| Compound | Structure | IC$_{50}$ in FP assay with FLSN-MLL (μM) | Vendor/ Cat # | IC$_{50}$ in HTRF assay (μM) |
|---|---|---|---|---|
| 6G10_4 Compound 48 | 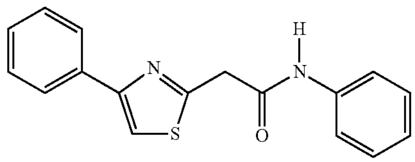 [SMILES: O=C(Cc1nc(-c2ccccc2)cs1)Nc1ccccc1] | NS, D 0.5 mM = 30% | Life Chemicals F1643-0298 | ND |
| 6G10_5 Compound 49 | 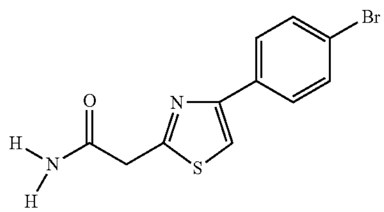 [SMILES: NC(=O)Cc1nc(-c2ccc(Br)cc2)cs1] | NS, D 1.0 mM = 10% | Sigma L119199 | ND |
| 6G10_6 Compound 50 | 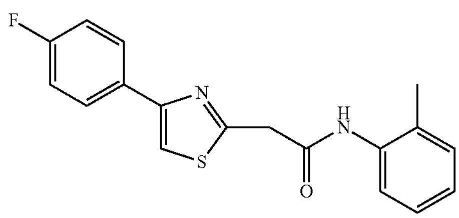 [SMILES: Cc1ccccc1NC(=O)Cc1nc(-c2ccc(F)cc2)cs1] | 122 | Enamine T5972333 | ND |
| 6G10_7 Compound 51 | 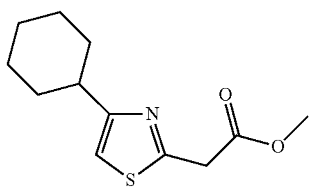 [SMILES: COC(=O)Cc1nc(C2CCCCC2)cs1] | 1900 | Enamine T5428144 | ND |
| 6G10_8 Compound 52 | 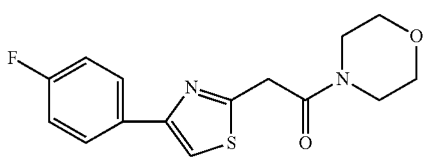 [SMILES: O=C(Cc1nc(-c2ccc(F)cc2)cs1)N1CCOCC1] | 107 | Enamine T5709338 | ND |
| 6G10_9 Compound 53 | 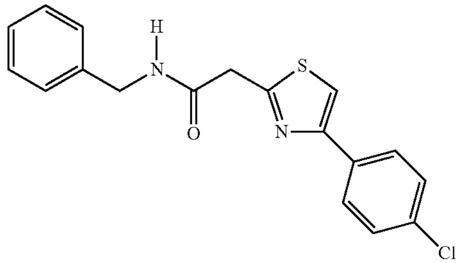 [SMILES: O=C(Cc1nc(-c2ccc(Cl)cc2)cs1)NCc1ccccc1] | 1060 | Enamine T5882535 | ND |
| 6G10_10 Compound 54 | 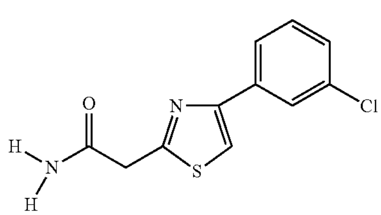 [SMILES: NC(=O)Cc1nc(-c2cccc(Br)c2)cs1] | 137 | Enamine T5668711 | ND |

TABLE 4-continued

Structures and activities of hits from MFL and 6G10 analogues measured by FP and HTRF.

| Compound | Structure | IC$_{50}$ in FP assay with FLSN-MLL (μM) | Vendor/ Cat # | IC$_{50}$ in HTRF assay (μM) |
|---|---|---|---|---|
| 6G10_11 Compound 55 | 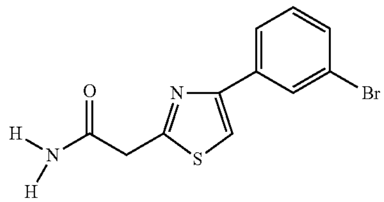 | NA | Enamine T5670346 | ND |
| 6G10_12 Compound 56 | 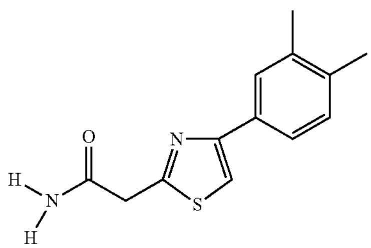 [SMILES: Cc1ccc(-c2csc(CC(N)=O)n2)cc1C] | NS, D 0.5 mM = 30% | Enamine T5657444 | ND |
| 6G10_13 Compound 57 | 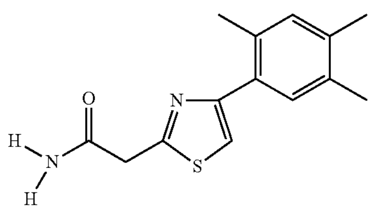 [SMILES: Cc1cc(C)c(-c2csc(CC(N)=O)n2)cc1C] | 1200 | Enamine T5665037 | ND |
| 6G10_14 Compound 58 | 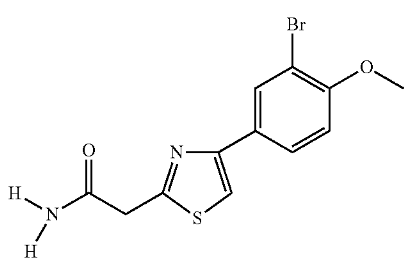 [SMILES: COc1ccc(-c2csc(CC(N)=O)n2)cc1Br] | 80 | Enamine T5647112 | ND |
| 6G10_15 Compound 59 | 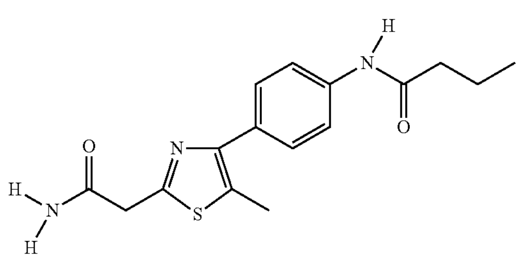 [SMILES: CCCC(=O)Nc1ccc(-c2nc(CC(N)=O)sc2C)cc1] | 830 | Enamine T5665035 | ND |

NA—no activity,
ND—not determined.

What is claimed is:

1. A pharmaceutical preparation comprising a compound having the structure or pharmaceutically acceptable salts of thereof:

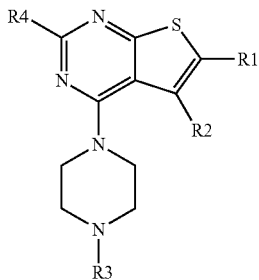

wherein R3 is:

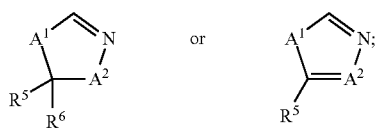

R1, R2, R4, R5, and/or R6 independently comprise: H, substituted or non-substituted alkyl, substituted or non-substituted alkoxy, a halogen, a ketone, a carbocyclic ring, an aromatic ring, a heterocyclic aromatic ring comprising carbon and one or more nitrogen, oxygen and/or sulfur members which may be non-substituted or substituted with substituted or non-substituted alkyl, aryl, halogen, hydrogen bond donor or acceptor, a heterocyclic non-aromatic ring comprising carbon and one or more nitrogen, oxygen and/or sulfur members which may be non-substituted or substituted with alkyl, aryl, halogen, hydrogen bond donor or acceptor, carbocyclic aromatic or non-aromatic ring fused or attached to the thienopyrimidine ring system non-substituted or substituted with alkyl, aryl, halogen, hydrogen bond donor or acceptor, carbocyclic or heterocyclic aromatic ring comprising carbon atoms and one or more nitrogen, oxygen and/or sulfur members fused to another aromatic ring, or a hydrogen bond donor or a hydrogen bond acceptor; and wherein A1 and A2 are independently selected from carbon, nitrogen, sulfur, or oxygen;

wherein said compound is not Compound 1 as disclosed in Table 1.

2. The pharmaceutical preparation of claim 1, wherein said structure is Compound 4 as disclosed in Table 1.

3. The pharmaceutical preparation of claim 1, wherein said structure is selected from the group consisting of Compounds 4, 5, 12, 14-17, 20-21, 31, 64-68, and 70-72 as disclosed in Table 1.

4. A method comprising administering a composition of claim 1 to a subject.

5. The method of claim 4, wherein said subject is a human.

6. The method of claim 4, wherein said subject is non-human animal.

7. The method of claim 5, wherein said human is suffering from leukemia.

8. The method of claim 7, wherein said leukemia comprises AML or ALL.

9. A method of inhibiting the interaction of MLL and menin
comprising administering a compound of claim 1 to a sample comprising MLL or MLL fusion protein and menin.

10. The method of claim 9, wherein said composition comprises a compound selected from the group consisting of Compounds 1, 4, 5, 12, 14-17, 20-21, 31, 64-68, and 70-72 as disclosed in Table 1.

* * * * *